US012591967B2

(12) United States Patent
De Bruijn et al.

(10) Patent No.: US 12,591,967 B2
(45) Date of Patent: Mar. 31, 2026

(54) DISPLACEMENT ESTIMATION OF INTERVENTIONAL DEVICES

(71) Applicant: KONINKLIJKE PHILIPS N.V., Eindhoven (NL)

(72) Inventors: Frederik Jan De Bruijn, Eindhoven (NL); Jinhui Qian, Eindhoven (NL); Harold Agnes Wilhelmus Schmeitz, Eindhoven (NL); Bart Jacob Bakker, Eindhoven (NL); Ruud Johannes Gerardus Van Sloun, Eindhoven (NL); Gerhardus Wilhelmus Lucassen, Eindhoven (NL); Vincent Maurice André Auvray, Meudon (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 264 days.

(21) Appl. No.: 18/276,568

(22) PCT Filed: Feb. 4, 2022

(86) PCT No.: PCT/EP2022/052746
§ 371 (c)(1),
(2) Date: Aug. 9, 2023

(87) PCT Pub. No.: WO2022/171539
PCT Pub. Date: Aug. 18, 2022

(65) Prior Publication Data
US 2024/0169522 A1     May 23, 2024

(30) Foreign Application Priority Data
Feb. 12, 2021     (EP) ..................................... 21290006

(51) Int. Cl.
*G06T 7/00*        (2017.01)
*A61B 8/00*        (2006.01)

(52) U.S. Cl.
CPC .......... *G06T 7/0012* (2013.01); *A61B 8/4245* (2013.01); *G06T 2207/10116* (2013.01);
(Continued)

(58) Field of Classification Search
CPC ......... G06T 7/0012; G06T 2207/10116; G06T 2207/20081; G06T 2207/20084;
(Continued)

(56) References Cited

U.S. PATENT DOCUMENTS 11,604,249 B2 * 3/2023 Stapert ..................... A61B 8/12
11,839,509 B2 * 12/2023 Gijsbers .............. A61B 8/0841
(Continued)

FOREIGN PATENT DOCUMENTS

EP        3705049 A1     9/2020
WO    2017102340 A1     6/2017
WO    2019048482 A1     3/2019

OTHER PUBLICATIONS

International Search Report and Written Opinion of PCT/EP2022/052746, dated Apr. 7, 2022.
(Continued)

*Primary Examiner* — Tom Y Lu

(57)        ABSTRACT

A system is provided for determining the movement of an interventional device inside a lumen. The interventional device comprises a distal portion inside the lumen and a proximal portion outside the lumen and the system comprises a processor. The processor is configured to receive one or more images from an ultrasound transducer, wherein the images are representative of the lumen with the interventional device inside and input the one or more images into a machine learning algorithm. The machine learning algorithm is trained to learn the relationship between the content of one or more images of an interventional device inside a lumen and the displacement of the distal portion of
(Continued)

102        104 the interventional device in an elevational direction parallel, or almost parallel, to the direction of movement of the distal portion of the interventional device and output a one dimensional estimated displacement corresponding to the movement of the distal portion of the interventional device in the elevational direction for one or more of the images.

15 Claims, 15 Drawing Sheets

(52) U.S. Cl.
    CPC .............. *G06T 2207/20081* (2013.01); *G06T 2207/20084* (2013.01)

(58) Field of Classification Search
    CPC ... A61B 8/4245; A61B 8/0891; A61B 8/4254; A61B 8/52; A61B 8/12
    See application file for complete search history.

(56) References Cited

U.S. PATENT DOCUMENTS

| | | | | |
|---|---|---|---|---|
| 11,986,339 | B2 * | 5/2024 | Megens | ............... A61B 8/4245 |
| 12,220,275 | B2 * | 2/2025 | Kim | ...................... A61B 8/085 |
| 2018/0360417 | A1 | 12/2018 | Henneken | |
| 2020/0129143 | A1 | 4/2020 | Di Tullio | |

OTHER PUBLICATIONS

Prevost, Raphael et al "Deep Learning for Sensorless 3D Freehand Ultrasound Imaging", Medical Image Computing and Computer-Assisted Intervention—MICCAI 2017, pp. 628-636.

Prevost, Raphael et al, "3D freehand ultrasound without external tracking using deep learning", Medical Image Analysis, vol. 48, pp. 187-202, Aug. 2018.

Wagner, Robert F. et al, "Statistics of speckle in ultrasound B-Scans", IEEE Transactions on Sonics and Ultrasonics, vol. 30, No. 3, pp. 156-163, May 1983.

Talou, Gonzalo D. Maso, "Registration methods for IVUS: Transversal and longitudinal transducer motion compensation", IEEE Transactions on Biomedical Engineering, vol. 64, No. 4, pp. 890-903, Apr. 2017.

Gee, A.H. et al, Sensorless freehand 3D ultrasound in real tissue: speckle decorrelation without fully developed speckle, Technical Report CUED/F-INFENG/TR 510, Cambridge University, Department of Engineering, Jan. 2005.

Arbab-Zadeh, Armin et al, "Axial movement of the intravascular ultrasound probe during the cardiac cycle: Implications for threedimensional reconstruction and measurements of coronary dimensions", American Heart Journal, vol. 138, No. 5, pp. 865-872, Nov. 1999.

\* cited by examiner 102        104

202        204

First System

First Position Estimates

Combiner        210

Second System

Estimated Displacement

Second Position Estimate        212

206        208 a)

b)

a)

b)

| A | B | C | D | E | F | G | H |
|---|---|---|---|---|---|---|---|
| I | J | K | L | M | N | O | P |

Sector 01
Displacement indicator 02

Pullback path 03
Images 04 and 05
Sectorwise displacements 06 and 07
Larger displacement on outside of curve Circular vessel 08
Centerline 09
Pullback path 010
Oblique IVUS image 011
Perpendicular to centerline 012

104 ultrasound array radiopaque markers

DISPLACEMENT ESTIMATION OF INTERVENTIONAL DEVICES

CROSS-REFERENCE TO PRIOR APPLICATIONS

This application is the U.S. National Phase application under 35 U.S.C. § 371 of International Application No. PCT/EP2022/052746, filed on Feb. 4, 2022, which claims the benefit of European Patent Application No. 21290006.2 filed on Feb. 12, 2021. These applications are hereby incorporated by reference herein.

FIELD OF THE INVENTION

The invention relates to the field of movement of an interventional device. In particular, the invention relates to the field of estimating the displacement of an interventional device inside a lumen based on ultrasound images.

BACKGROUND OF THE INVENTION

Intravascular ultrasound (IVUS) imaging is a technology that uses ultrasound to image blood vessels from within the vessel, providing a 360° view from the position of the ultrasound device that is placed at the tip of a catheter. At each catheter position, a two-dimensional (2D) image is acquired that contains the vessel lumen, the vessel wall and some adjacent structures beyond. In case of a vascular disease, the images also reveal the composition and spatial distribution of malignant tissue, e.g. calcium and thrombus.

By acquiring a sequence of IVUS images during a catheter pullback, in principle, one acquires a 3D volumetric data set of the vessel including the diseased and often stenosed sections. In order to treat the impaired blood flow, the physician usually needs to measure the stenosed, and potentially desired, lumen area, the longitudinal extent of the disease and the location of any side branches to determine the length of the section to be treated. These measurements are used to determine the diameter and length of the appropriate balloon or appropriate stent.

Rotational IVUS catheters are similar to optical coherence tomography (OCT) catheters, to the extent that both provide a motorized pullback in addition to the motorized transducer rotation. This is why rotational IVUS, and OCT, catheters enable the provision of both the diameter and the length of the diseased vascular section.

However, phased-array IVUS catheters do not need any motorization at all. In fact, physicians widely prefer to retract the catheter manually. Unfortunately, they do so with an unknown and generally time-varying speed, preventing adequate 3D assessment.

The physician's preference for manual pullback as well as the presence of cardiac-induced transducer motion and motion reversal cause a loss of distance information in the direction of the pullback. This distance information is vital for proper interpretation of the IVUS data both for physicians and for automated detection and quantification algorithms.

Current methods for estimating the motion of a catheter inside a lumen expect a motorized, constant pullback velocity and only focus on cardiac-induced motion reversal of the catheter. Furthermore, these methods also require the data to be split in cardiac phases (either by ECG-based or image-based gating) and the use of a steady phase as a reference.

Current methods also need a large temporal search window in order to find the correct 'similar' frame within a sufficiently large number of previous frames; an operation that is computationally expensive. Thus, there is a need for an improved method for estimating the motion of a catheter inside a lumen.

SUMMARY OF THE INVENTION

The invention is defined by the claims.

According to examples in accordance with an aspect of the invention, there is provided a system for determining the displacement of an interventional device inside a lumen, the interventional device comprising a distal portion inside the lumen and a proximal portion outside the lumen, the system comprising:

a processor configured to:

receive one or more images from an ultrasound transducer, wherein the images are representative of the lumen; and input the one or more images into a machine learning algorithm.

The machine learning algorithm is trained to learn the relationship between the content of one or more images of a lumen and the displacement of the distal portion of an interventional device in an elevational direction substantially perpendicular to the imaging plane of the ultrasound transducer. The machine learning algorithm is trained thus to determine a relationship between the one or more images of the lumen acquired with the ultrasound transducer on the distal portion of the interventional device and the displacement of the interventional device when those one or more images of the lumen have been acquired. Further, the machine learning algorithm is configured to output a one dimensional estimated displacement corresponding to the motion of the distal portion of the interventional device in the lumen for one or more of the images. The interventional device may be one of a catheter, a guidewire, a sheath or a combination of those. The interventional device may be also referred to as intraluminal device or intravascular device, depending on the clinical application it is used for. The distal portion may be the distal end of the interventional device in some embodiments. The proximal portion may be the proximal end of the interventional device in some embodiments.

The motion or movement of objects can be quantified by their displacement, where the magnitude and the direction of the displacement are specified. However, determining the displacement of an object in 3D requires calculating three variables, which can be computationally intensive and increase the time required to perform the calculation. In applications where the motion of an object is required in real time, the calculation of the displacement may not be feasible.

The inventors have realized that, for the motion of interventional devices in a lumen, the interventional device is constrained to move in one dimension (i.e. in the longitudinal direction of the vessel, hence the elevational direction of the ultrasound imaging system). Thus, even if the interventional device is constantly changing direction in typical coordinate systems (e.g. Cartesian), the interventional device is always travelling in one direction relative to the lumen.

The need to estimate displacement only in one dimension simplifies the estimation process thus improving the robustness of the machine learning algorithm and could even reduce/remove the effects of compounding errors. In other words, the simplification of the estimation process by the machine learning algorithm can improve the accuracy and/or precision of the output one dimensional estimated displacements due to reduced complexity.

The displacement of the interventional device in the lumen can be determined by training a machine learning algorithm to learn the relationship between ultrasound images of the lumen with an interventional device inside and the displacement of the interventional device in the lumen. This is possible due to the "speckle" pattern of ultrasound images and its relative stability. The speckle pattern extends in three dimensions and thus, in consecutive ultrasound images, it should be relatively stable, i.e. without significant change over time.

However, if the speed of the interventional device is varied, the speckle pattern will become stretched and compressed when the images are arranged at uniform time intervals. A machine learning algorithm can be trained to learn the relationship between the speckle patterns on the images and the displacement of the distal portion of the interventional device between ultrasound images provided by an ultrasound transducer.

As the machine learning algorithm is configured to output a 1D displacement value, the time required for a processor to perform the calculations required for the machine learning algorithm can be significantly reduced and thus it is possible to determine the displacement of the distal portion of the interventional device in the lumen in real time.

Additionally, the machine learning algorithm will be more robust (i.e. improved accuracy/precision of outputs and/or reduced unexpected outputs) due to the simplification of the machine learning algorithm when compared to algorithms with three outputs (i.e. 3D displacements).

The ultrasound transducer may be an intravascular ultrasound transducer disposed at or near the distal portion of the interventional device.

Each of the one or more images may have a corresponding acquisition time (i.e. point in time) and the processor may be further configured to determine an estimate of the speed of the distal portion of the interventional device based on the estimated displacement and the difference in the acquisition time between the images.

The processor may be further configured to determine the position of the interventional device in the lumen based on the one or more images and the displacement of the interventional device.

For example, the displacement between two images can be used to determine the position of the interventional device within the lumen at the moment that each image is taken. Thus, the position of the interventional device can be mapped on, for example, a model of the lumen from an external view.

The machine learning algorithm may be further configured to output a motion reversal indication, wherein the motion reversal indication indicates a change in the direction of the motion within the lumen.

Motion reversal can be quantified based on, for example, the sign of the output displacement. If the displacement is negative, this could indicate the interventional device is moving backwards. Alternatively, the machine learning algorithm could output an additional variable where "0" indicates normal motion and "1" indicates motion reversal.

The machine learning algorithm may be configured to output the estimated displacement in at most 0.2 seconds from the one or more images being input into the machine learning algorithm.

A time of at most 0.2 seconds would allow the machine learning algorithm to output displacement estimates five times per second. Preferably, the machine learning algorithm can output displacement estimates at least 10 times per second.

The processor may be further configured to determine a speed limit indication based on whether the estimated displacement is higher than a predetermined value.

If the interventional device is moving too fast, the intravascular ultrasound transducer may not be able to take enough images for an accurate representation of the lumen. Thus, the processor can be configured to determine a speed limit indication when the displacement between images is higher than a pre-determined value (e.g. 0.23 mm; at 30 fps, resulting in a speed limit of 7 mm/s). Additionally, the processor may be configured to alert a user if the interventional device is being pulled too fast (e.g. if the speed limit indications is "too fast").

Alternatively, the system may be further configured to calculate an estimated speed from the estimated displacement and the time between obtaining estimated displacements from the machine learning algorithm. The value of the estimated speed may then be used to determine the speed limit indication.

The machine learning algorithm may be based on one or more of:

a fully connected neural network;

a convolutional neural network;

a recurrent neural network; or a long short term memory, LSTM, based neural network.

One or more images may be input into the machine learning algorithm in polar coordinates.

The processor may be further configured to determine a median displacement indication from a plurality of estimated displacements corresponding to consecutive images or consecutive (corresponding) image regions.

The processor may be further configured to input cardiac phase data into the machine learning algorithm, wherein the cardiac phase data is representative of a subject's cardiac cycle.

It may be beneficial to include cardiac phase data to ensure that any changes in the lumen due to the cardiac cycle are taken into account by the machine learning algorithm.

The system may further comprise a memory buffer for storing the one or more images and/or storing one or more estimated displacements.

The system may further comprise a user interface for displaying the one or more images and the corresponding estimated displacements.

The invention also provides a method for determining the motion of an interventional device inside a lumen, the interventional device comprising a distal portion inside the lumen and a proximal portion outside the lumen wherein the interventional device comprises an intravascular ultrasound transducer at or near the distal portion of the interventional device, the method comprising:

receiving one or more images from an intravascular ultrasound transducer, wherein the images are representative of the lumen with the interventional device inside; and inputting the one or more images into a machine learning algorithm.

The machine learning algorithm is trained to learn the relationship between the content of one or more images of a lumen and the displacement of the distal portion of an interventional device in an elevational direction substantially perpendicular to the imaging plane of the ultrasound transducer. The machine learning algorithm is trained thus to determine a relationship between the one or more images of the lumen acquired with the ultrasound transducer on the distal portion of the interventional device and the displacement of the interventional device when those one or more images of the lumen have been acquired. Further, the machine learning algorithm is configured to output a one dimensional estimated displacement corresponding to the motion of the distal portion of the interventional device in the lumen for one or more of the images.

The invention also provides a computer program product comprising computer program code means which, when executed on a computing device having a processing system, cause the processing system to perform all of the steps of the method for determining the motion of a interventional device inside a lumen.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
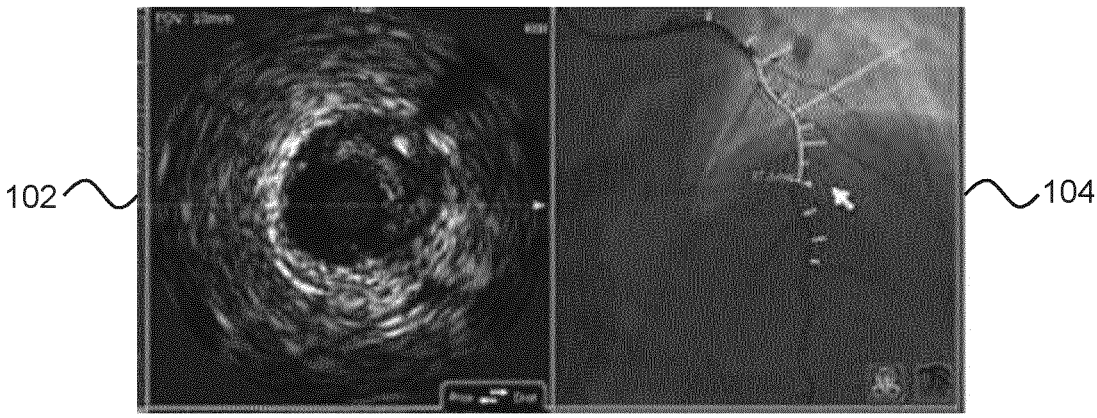
FIG. 1 shows an example output screen of a co-registration (COREG) system with an IVUS image and an X-ray image showing a pullback trajectory for an interventional device.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Although the invention is exemplified in the description for a catheter, in any of the embodiments the interventional device may be one of a catheter, a guidewire, a sheath or a combination of those. Although in the exemplary description of the invention the wording distal end and proximal end is used, in any of the embodiments this can be interpreted as distal portion and proximal portion of the interventional device, as it is also contemplated.

The invention provides a system for determining the motion or movement of a catheter inside a lumen. The catheter comprises a distal end inside the lumen and a proximal end outside the lumen and the system comprises a processor. The processor is configured to receive one or more images from an ultrasound transducer, wherein the images are representative of the lumen with the catheter inside and input the one or more images into a machine learning algorithm. The machine learning algorithm is trained to learn the relationship between the content of one or more images of a catheter inside a lumen and the displacement of the distal end of the catheter in an elevational direction parallel, or almost parallel, to the direction of motion of the distal end of the catheter and output a one dimensional estimated displacement corresponding to the motion of the distal end of the catheter in the elevational direction for one or more of the images.

FIG. 1 shows an example output screen of a co-registration, COREG, system with an IVUS image 102 and an X-ray image 104 showing a pullback trajectory for a catheter. Until recently, X-ray fluoroscopy was the only option to obtain an estimate of the longitudinal displacement of a phased-array IVUS transducer relative to the vessel wall along the pullback trajectory.

However, recently a system has been developed to estimate the speed/displacement of the tip of the catheter that is fully based on the ultrasound images. This new method, disclosed below, provides an estimate of the elevational speed (i.e. the displacement between consecutive frames) of the IVUS transducer relative to the vessel wall and is based on the use of an machine learning algorithms.

Both the X-ray based position estimate method and the IVUS based displacement estimation have their specific strengths and shortcomings. However, both methods can be combined synergistically in order to significantly reduce the shortcoming of both methods.

Currently, the frame rate of the X-ray system must be sufficiently high to ensure an appropriately dense sequence of position estimates to calculate a sufficiently accurate position estimate for each of the simultaneously acquired IVUS image 102. This currently leads to a continuous exposure of ionizing radiation. By combining the X-ray and IVUS methods for position estimation and displacement estimation respectively, the need for continuous X-ray acquisition is overcome and thus the exposure of ionizing radiation is reduced.

Additionally, in current COREG systems, a sequence of transducer position estimates from the X-ray images 104 is not available in real-time and requires the full sequence of X-ray images 104 to be available. Instead, the displacement estimates from IVUS images 102 are generally available with a relatively small latency (i.e. typically of a few frames). Thus, a combination of both the X-ray position estimates and the IVUS displacement estimates can reduce the computational load and speed up the calculation of transducer position estimates.

The accuracy of position estimates that are acquired from X-ray images 104 are typically subject to the spatial resolution of the X-ray acquisition system. In practice, this leads to an accuracy of about 2 mm in the elevational position estimates (i.e. the position along the length of the lumen). Moreover, the accuracy of position estimates that are acquired from X-ray images 104 can also be subject to motion blur by the X-ray system. In some cases the characteristics of this motion blur may not be available to the position estimation process. Advantageously, the absolute error in IVUS-based displacement estimates reaches values of about 0.1 mm/s. Thus, a combination of both the X-ray position estimate and the IVUS displacement estimate can provide position estimates with robustness and accuracy that is higher than any of the separate systems.

Figure 2:
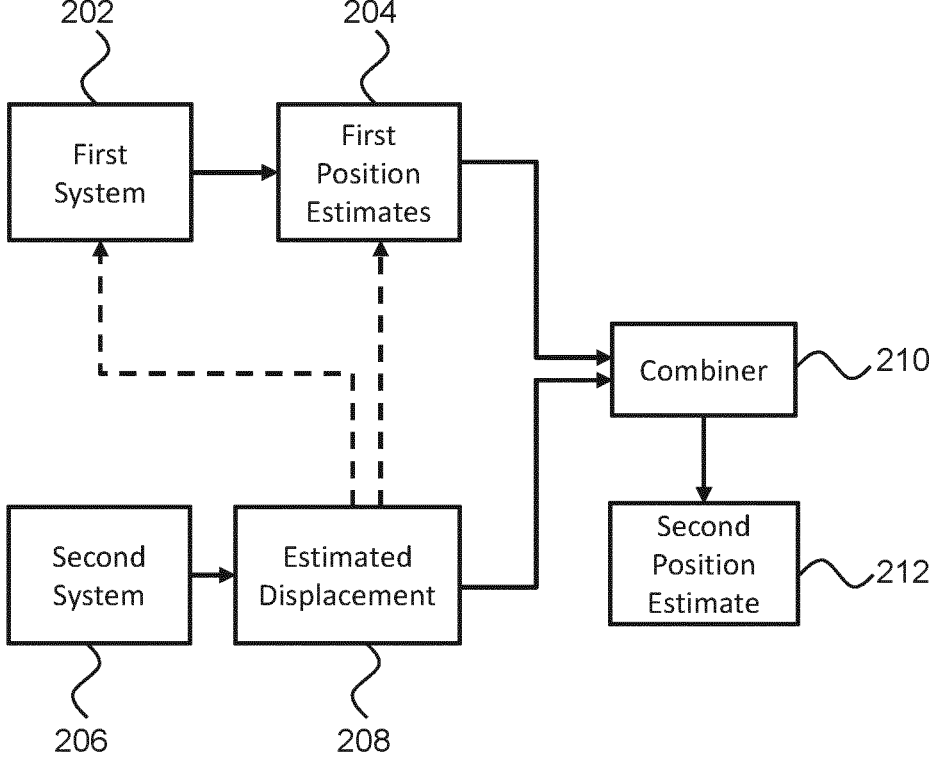
FIG. 2 shows a first method for estimating the displacement of an interventional device in a lumen.

FIG. 2 shows a first method for estimating the displacement of a catheter in a lumen. The X-ray-based position estimation process, such as, but not limited to, the one that already exists as part of the aforementioned COREG system, forms a first system 202 that provides a sequence of first position estimates 204 of the tip of the catheter. The X-ray system 202 provides one or more of X-ray images 104 which are used to determine the first position estimates 204.

The IVUS-based displacement estimation system forms a second system 206 that provides a sequence of estimated displacement values 208. The IVUS system 206 provides one or more IVUS images 102 which are used to determine the estimated displacement between the IVUS images. Additionally, the speed of the tip of the catheter can be estimated based on the estimated displacements 208 and the time taken between IVUS images (e.g. from image timestamps).

A 'combiner' element 210 uses the sequence of first position estimates 204 and the sequence of estimated displacements 208 (or a sequence of speed estimates) to calculate a sequence of improved, second position estimates 212.

Additionally, the estimated displacements 208 and/or estimated speed can be used to influence the X-ray acquisition process. The estimated displacement 208 and/or estimated speed can also be used to aid the first positon estimation 204.

Figure 3:
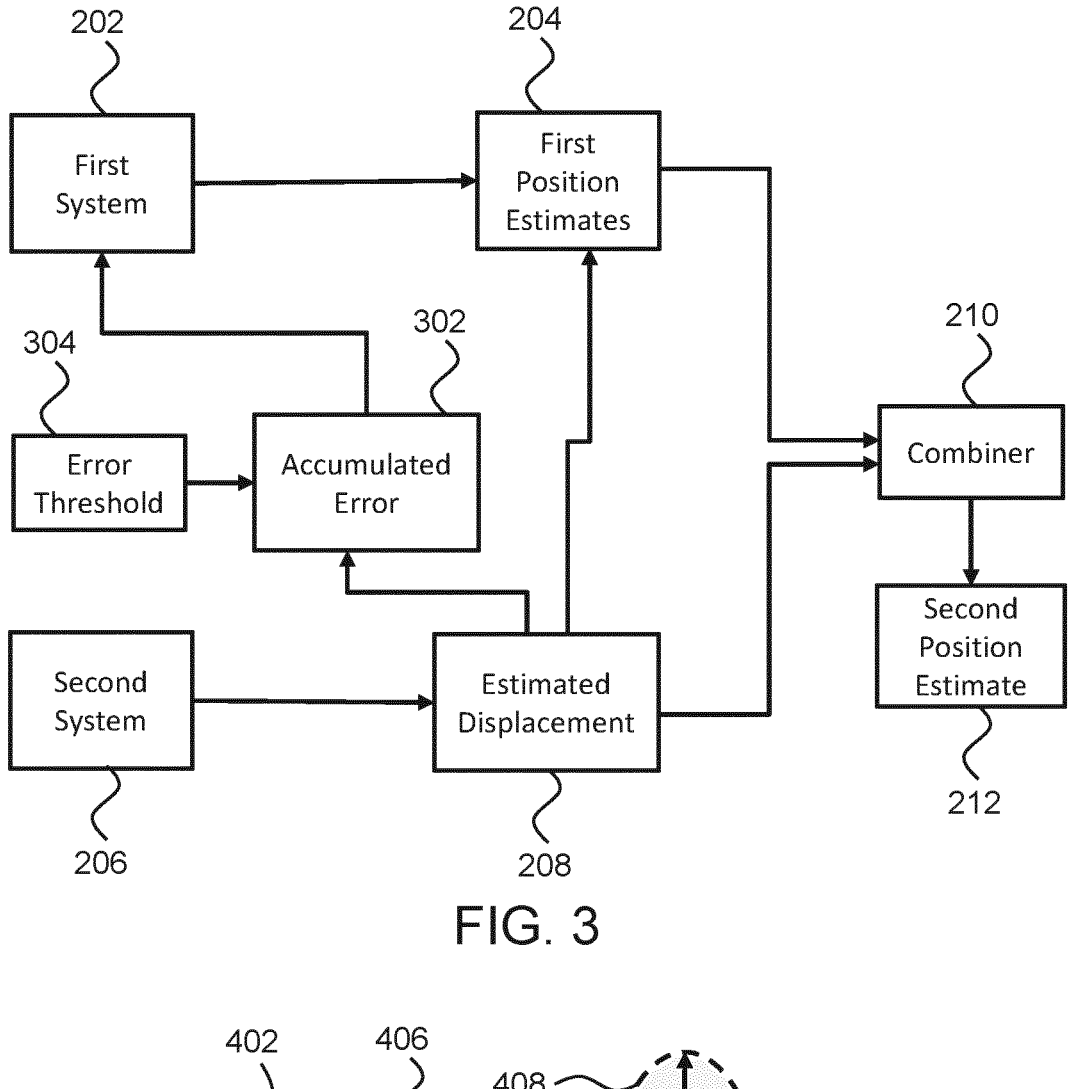
FIG. 3 shows a second method for estimating the displacement of an interventional device in a lumen.

FIG. 3 shows a second method for estimating the displacement of a catheter in a lumen. The known accuracy of the sequence of estimated displacements 208 can be used to estimate the accumulated error 302 in the second sequence of position estimates 212 that follows from the sum of the estimated displacement 208 (or the numerical integration of the estimated speed values). For every IVUS image 102, the value of the accumulated error 302 is continuously compared to a predetermined threshold value 304, and a resulting signal is provided to the first system 202 which is used to determine when to acquire a new first position estimate 204. This lowers the number of required first position estimates 204 and thus lowers the number of required X-ray images 104. The number of required X-ray images 104 can be as low as the number of required first position estimates 204. However, the number of required X-ray images 104 may be higher should this be necessary for a reliable estimation of the position.

If the average/expected error per image 102 is known, or can be estimated, the expected error after N images/frames can further be estimated. The average/expected error may be dependent on the estimated displacement values 208. The expected error after N frames may be more forgiving then the sum of the expected errors since the errors are likely a combination of over- and under estimations cancelling each other out. For example, in the case where the error in each of the displacements is $e_i$, where the errors $e_i$ are assumed to be normally distributed with zero mean, the accumulated error $e_{acc}$ may be square root of the sum of the errors $e_i$ squared:

$$e_{acc} = \sqrt{\sum_{i=1}^{N} e_i^2}$$

The combination of the first system 202 and the second system 206 could also use the ability of the second system 206 to detect an absence of catheter motion (e.g. when the transducer is 'parked' for multiple frames by the operator). Here, the sequence of estimated displacements 208 would be compared to a predetermined threshold value to test whether the absolute displacement is sufficiently low to indicate a 'standstill'. The estimated speed may also be used to determine whether the catheter is still.

Optionally, or additionally, the number of consecutive IVUS images that have been flagged as 'standstill' can be compared to a predetermined second threshold value to test when the number of standstill frames exceeds a predetermined value in order to indicate that the transducer is 'parked', upon which the first system can receive a signal that there is no immediate need for new first position estimates 204, thus lowering the number of required X-ray images 104.

The combined system could also use the ability of the second system 206 to detect that a predetermined maximum speed limit of the catheter along the elevational direction has been exceeded (e.g. when the catheter is pulled back too fast by the operator). In this situation, the first system 206 could receive a signal that the second system 202 cannot provide reliable displacement estimates 208, upon which the first system 202 increases the rate of first position estimates 204, therefore also raising the X-ray imaging framerate.

The sequence of estimated displacements 208 and/or speed estimates can also be made available for determining the first position estimate 204. For instance, the estimated displacements 208 can decrease the size of a search window in the first position estimation process due to the first system 202 'knowing' that the catheter position in a new X-ray image cannot be far from the previous position in the case where the estimated displacement 208 (or speed) is low. Alternatively, or additionally, the estimated displacements 208 can change the location of a search window in the first position estimation process, such that it is better centered on the most likely catheter position in a new X-ray image(s) 104.

Both the search-window size as well as the search-window position may be restricted by an estimate of the expected 'roadmap' of the catheter in the X-ray image 104 sequence. Such roadmap-estimate may be drawn manually, prior to the catheter pullback. Otherwise, new roadmap-hypotheses may be (re-)calculated automatically upon the acquisition of new X-ray images 104 and IVUS images 102. These example methods aim to reduce the number of calculations of the X-ray-based position estimation process, e.g. with the aim to have the first position estimates 204 earlier available during or after the pull-back acquisition, or even to alleviate the need for a completed X-ray sequence acquisition.

The estimated displacements 208 can also be used to improve the process of first position estimation from the X-ray images 104 by compensating for the motion-blur of the X-ray system 202. The motion-blur can be a combination of the exposure time of the first system 202 and of a build-in spatiotemporal image processing algorithm, generally with the aim to reduce noise. Although the point-spread function of the motion blur is dependent on the direction and magnitude of the motion, the blur process itself is due to an often constant temporal aperture. The first position estimation process improvement may include the explicit recovery of this temporal aperture, for example, based on a model and on estimation of the model parameters. Said first position estimation process improvement may also include the use of the recovered temporal aperture to reconstruct motion-blur free images, for example by way of deconvolution. Otherwise, said first position estimation process improvement may directly use the estimated displacements 208 (or the speed estimates) to recover the first position estimates 204 directly from one or more X-ray images, without explicit estimation of the temporal aperture. The implementation of such direct use of estimated displacements 208 may be based on a trained machine learning algorithm.

The estimated displacement 208 may also support the X-ray-based position estimation process in situations when the catheter trajectory does not stay sufficiently parallel to the imaging plane, for instance due to the vessel's tortuosity. In this case, the projection of the catheter in the X-ray image 104 is subject to perspective shortening, hampering the reliable recovery of the true travel distance through the vessel. Continuous availability of the displacement estimates 208 can be used to ensure position tracking in such cases when first position estimates 204 are locally unreliable or even absent. This may alleviate the need for a simultaneous secondary X-ray projection or even the need for a prior CT angiogram.

The projected catheter path length (in pixels) does not always linearly map to the real catheter path length (in mm). In the case where the vessel/lumen bends toward or away from the X-ray detector, the projected path length may be subject to perspective foreshortening. In such case, there is no longer a fixed linear relationship that can be used as a basis for moving a reduced search area in the X-ray image based on the IVUS-originated displacement estimates.

However, in the case where the catheter 402 comprises radiopaque markings, the varying relation between projected and real displacements can be derived from the varying distance between the markings in the (projected) X-ray image 104. As the transducer 404 is typically at the distal end of the catheter 402, a pullback causes the markings to precede the transducer 404 during many images and thus providing many 'calibration' samples. The calibration samples can be used to accurately estimate a locally varying relationship between projected and real catheter path length.

Alternatively, a prior CT model can be used to derive the 3D vessel shape and use this as a basis for correction for this perspective foreshortening.

The combiner element 210 may be a Kalman-filter based position estimator, which is a known approach in the fusion of different sensory measurements of different dynamic states of the same object (position, speed, acceleration). Alternatively, the combiner element may be a separate numerical integration element which calculates a third position estimate from the sequence of estimated displacements. The third position estimates and the sequence of first position estimates 204 can thus be used to determine the second, improved, position estimates 212. The combined system may also use time-interpolated first position estimates 204 from the first system 202 to compensate for the drift in the estimated displacements 208.

The second system 206 may be an extra-vascular ultrasound (EVUS) data instead of IVUS data. The EVUS data is typically acquired with an external ultrasound probe. Alternatively, the second system 206 may be external system that uses the externally (outside the body) measured elevational displacements 208 of the catheter as a proxy for the position and/or displacement of the transducer at, or near, the distal end of the catheter with respect to the imaged vessel.

The second system 206 may also be a combination of IVUS-based systems, EVUS-based systems and/or external catheter tracking methods.

The combined system can be applied to reduce total X-ray dose when the first system 202 is an X-ray imaging system. Furthermore, the invention can be used for a wide range of applications of elevational position estimation.

An application of the combined system is the accurate sizing of lesion/stent diameter and length. Current lesion/stent length estimations for manual IVUS pullback are read from an angiogram. The combined system can detect the catheter being temporarily parked during a pullback and subsequently invoke an indication to the operator. Additionally, the combined system may provide a signal to an algorithm to use multiple frames at the same location for an improved analysis. The multiple frames at the same location may be combine to improve the accuracy by combining multiple realizations of noise or of speckle, possibly under continued lateral tissue motion or under multiple realizations of blood speckle.

A particular implementation may be to use multiple frames, collected when the catheter is at a standstill, and use the difference in blood speckle between arteries and veins (caused by the differences in flow speed). This phenomenon has been observed in peripheral venous IVUS of the upper leg. Such algorithm may start automatically upon detecting the catheter being "parked".

Figure 4:
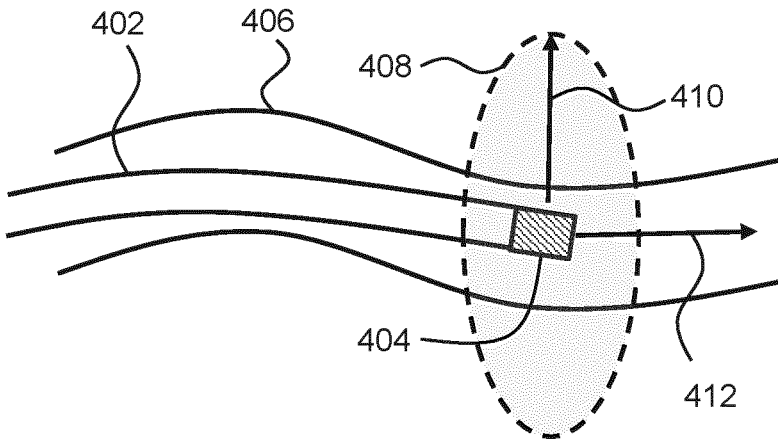
FIG. 4 shows an illustration of an interventional device in a lumen.

FIG. 4 shows an illustration of a catheter 402 in a lumen 406. In this example, the catheter 402 comprises an IVUS transducer 404 at the tip of the catheter 402 (i.e. at the distal end of the catheter 402). The IVUS transducer 404 has an imaging plane 408 which corresponds to the area imaged by the transducer 404 and which is perpendicular to the length of the transducer 404 and extends in a radial direction 410. The elevational direction 412 is defined as the direction perpendicular to the imaging plane 408 and thus is parallel, or almost parallel, to the direction of motion of the tip of the catheter 402. The elevational direction 412 may not always be parallel to the direction of travel as the tip of the catheter 402 may be at an angle when moving forward.

Figure 5:
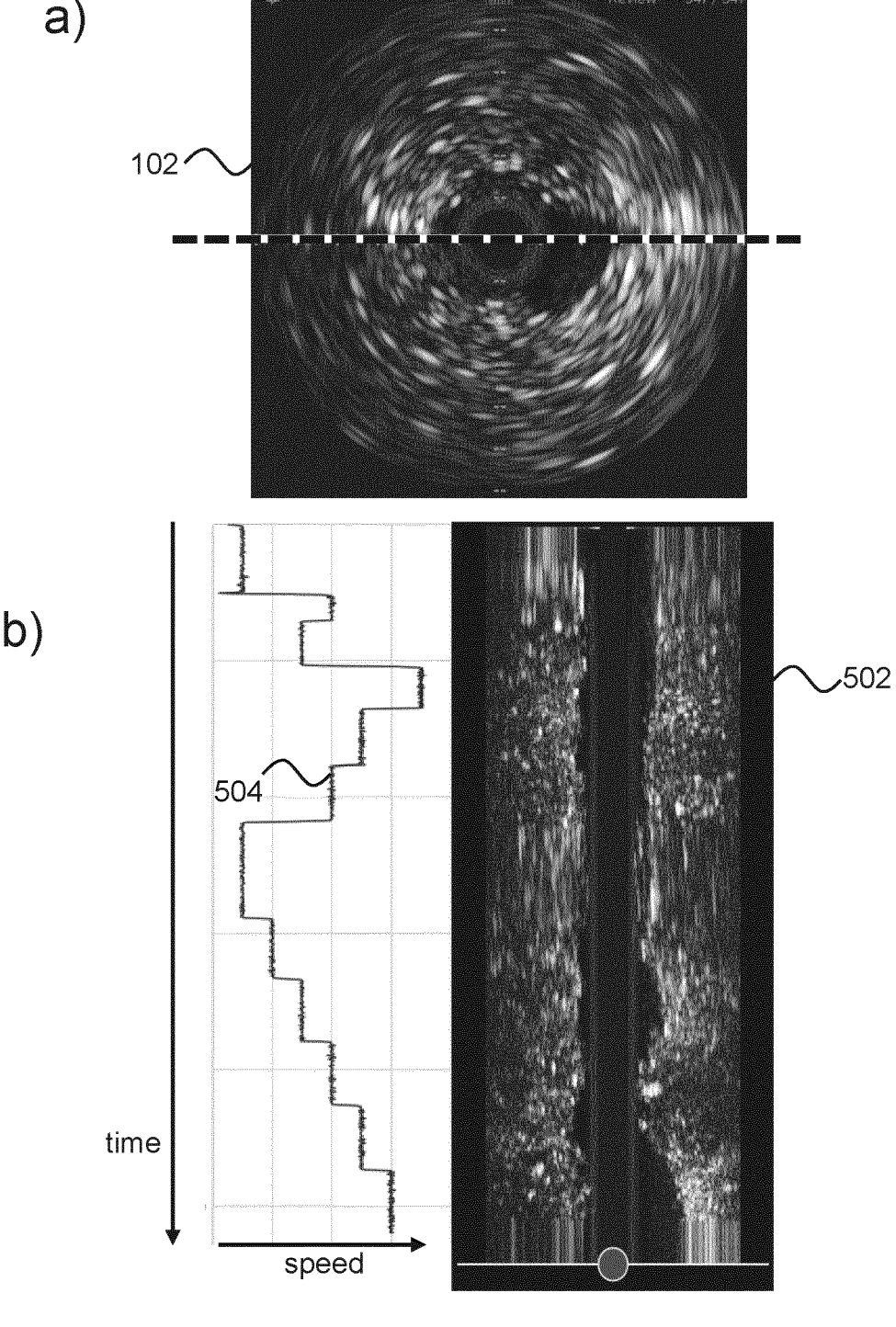
FIG. 5 shows images from an IVUS transducer in a lumen.

FIG. 5 shows images from an IVUS transducer 404 in a lumen 406. FIG. 5a shows a single image 102 from the transducer 404 and FIG. 5b shows a cross section of a sequence of consecutive IVUS images 502 with the corresponding speed values 504 of the tip of the catheter 402.

The image of FIG. 5b comprises a combination of a horizontal row of pixels from each of series of the images 102. One such horizontal row is shown as a dashed line in FIG. 5a, and the image of FIG. 5b is a vertical stack of such image rows.

It is possible to estimate the speed of the tip of the catheter 402 from the sequence of consecutive IVUS images 502.

The effect of speed variations on IVUS image data can be seen in FIG. 5. The IVUS image 102 in FIG. 5a clearly exhibits 'speckle', the notorious granular pattern that is typical to coherent imaging methods and therefore also to ultrasonography. An important characteristic of speckle is the fact that it is relatively stable (i.e. the same 3D scene, imaged from the same location, will repeatedly create the same speckle pattern).

The speckle phenomenon extents in all three spatial directions where the shape and size of the average speckle granule is governed by the ultrasound frequency and by the (limited) dimensions of the ultrasound transducer elements. It is therefore known to be relatively independent of the scattering tissue, provided that the distribution of acoustic scattering elements is sufficiently dense. Under these conditions it is expected that each of the speckles will adopt a relatively constant average shape and size in the elevational direction 412.

Under variations of the pullback speed, the shape of the recorded speckle pattern becomes stretched and compressed when images 102 are arranged at uniform time intervals. The apparent deformation of the spatial data is visible in FIG. 5b. The associated actual speed 504 is also depicted in FIG. 5b.

In addition to the variations in the magnitude of the velocity, the 'sign' of the velocity also tends to 'flip' occasionally, as the motion in the elevational direction 412 reverses within a single pullback. Motion reversal affects the monotonic spatial ordering of the images within the pullback sequence. Deliberate motion reversal generally occurs when a physician decides to revisit a previously captured site during the same pullback. Unintentional motion reversal is generally caused by cardiac motion and is therefore very common in IVUS imaging of the coronary arteries with transducer movements occasionally exceeding 6 mm between consecutive images.

Figure 6:
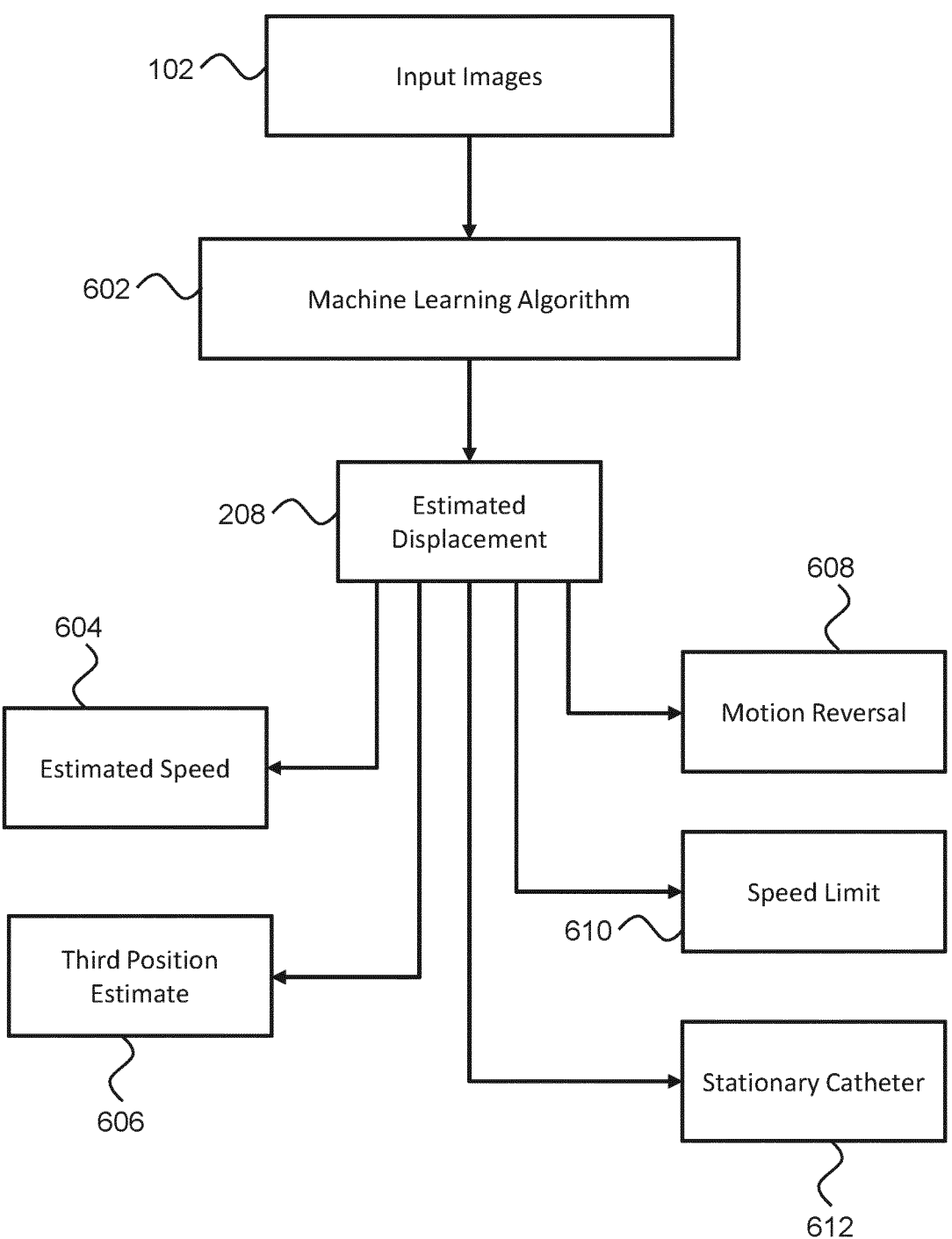
FIG. 6 shows a method for estimating the displacement of an interventional device in a lumen.

FIG. 6 shows a method for estimating the displacement 208 of a catheter in a lumen. One or more ultrasound images 102 (e.g. IVUS images) are input into a machine learning algorithm 602 which returns an estimate of the relative elevational displacement 208 associated with the one or more input images 102. The input images 102 are preferably provided in the same order as the acquisition. A system for performing the method may comprise a memory buffer to store data associated with the one or more input images 102. The stored data can be the input images 102 or data that is derived from the input images 102.

The machine learning algorithm 602 may be, but is not limited to, a fully-connected network, a convolutional network or a recurrent neural network (such as a long-short-term-memory network). The machine learning algorithm 602 may also comprise multiple modular artificial neural networks that are specialized in various aspects of the displacement estimation task. The machine learning algorithm 602 is trained to output a one dimensional estimated displacement value 208 corresponding to the input images 102.

The output estimated displacements 208 may also be converted into estimated speed values 604 (based on the time between image frames) and/or into a third position estimate 606 of the tip of the catheter in the lumen.

For example, the machine learning algorithm 602 may be composed of a convolutional neural network (CNN) operating on a temporal stack of corresponding envelope-data segments stored in the polar domain. Such segment may correspond to an image sector in the Cartesian domain, in which the input images 102 are normally displayed. In the polar domain, the speckle statistics appear virtually space invariant and thus allows the task of displacement estimation to be distributed in multiple, but similar, estimation units. In this example, the sector-wise separation may be chosen to improve robustness against signal loss due to lumen bifurcations or acoustic shadowing, as well as strong localized acoustic responses such as those caused by secondary guidewires (often called 'buddy wires'). Even in the absence of such perturbations, the segment-based estimation can outperform displacement estimation with a single network.

The machine learning algorithm 602 can be used to provide an estimated displacement 208 even in the presence of lateral (translational or rotational) motion in the image plane (e.g. due to cardiac motion). The estimated displacement 208 can further be used to indicate whether a physician exceeds a predefined speed limit 610, and provide the indication to a user interface. The estimated displacement 208 can used be used to improve interpretation of a sequence measurements, for example, by providing a sequence of automated lumen-area measurements as a function of the physical pullback distance in mm instead of the sequential frame index.

Motion reversal 608 in the elevational direction 412 can also be detected based on the estimated displacement 208. The magnitude of inter-image displacement in the reverse motion direction can also be estimated at a computational cost that allows real-time detection and without cardiac gating.

The estimated displacement can also be used to detect the absence of catheter movement 612 (e.g. when the transducer is 'parked' for multiple frames by the operator). Here, the sequence of estimated displacements 208 can be compared to a predetermined threshold value to test whether the estimated displacement 208 is sufficiently low to indicate a 'standstill'. The estimated speed may also be used to determine whether the catheter is stationary 612.

Figure 7:
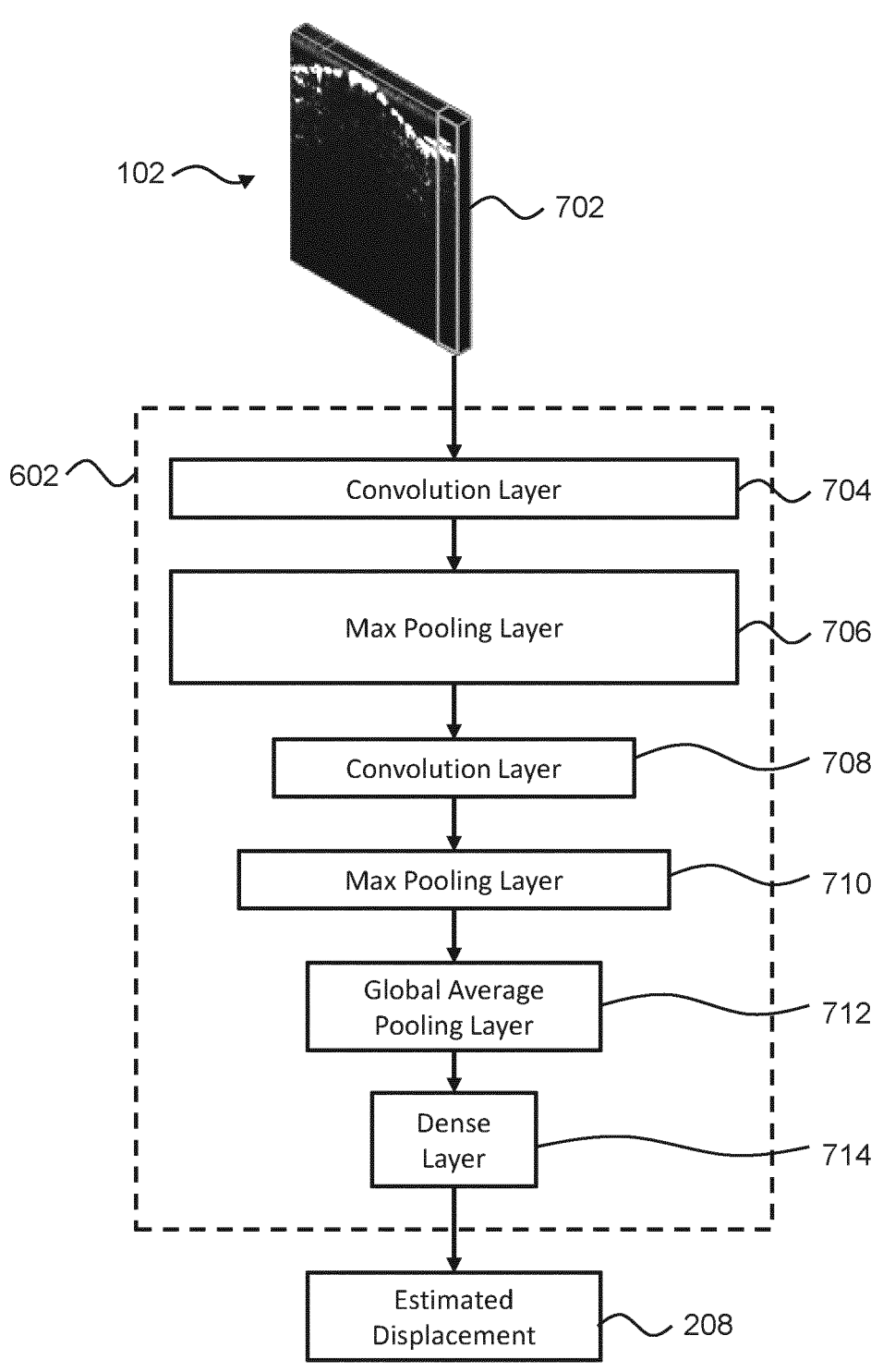
FIG. 7 shows an example architecture for the machine learning algorithm.

FIG. 7 shows an example architecture for the machine learning algorithm 602. The image 102 is a polar IVUS image composed of 256 lines. In this example, the image 102 is split into eight segments 702 of 32 lines each and the segments 702 are input separately into the machine learning algorithm 602. Each segment 702 is passed through a first convolutional layer 704, a first max pooling layer 706, a second convolutional layer 708, a second max pooling layer 710, a global average pooling layer 712 and one or more dense layers 714. The dense layers 714 output an estimated displacement 208 for each one of the segments 702. The estimated displacements 208 from each one of the segments 702 can then be combined (e.g. average or median) to obtain a combined estimated displacement which is more robust.

Figure 8:
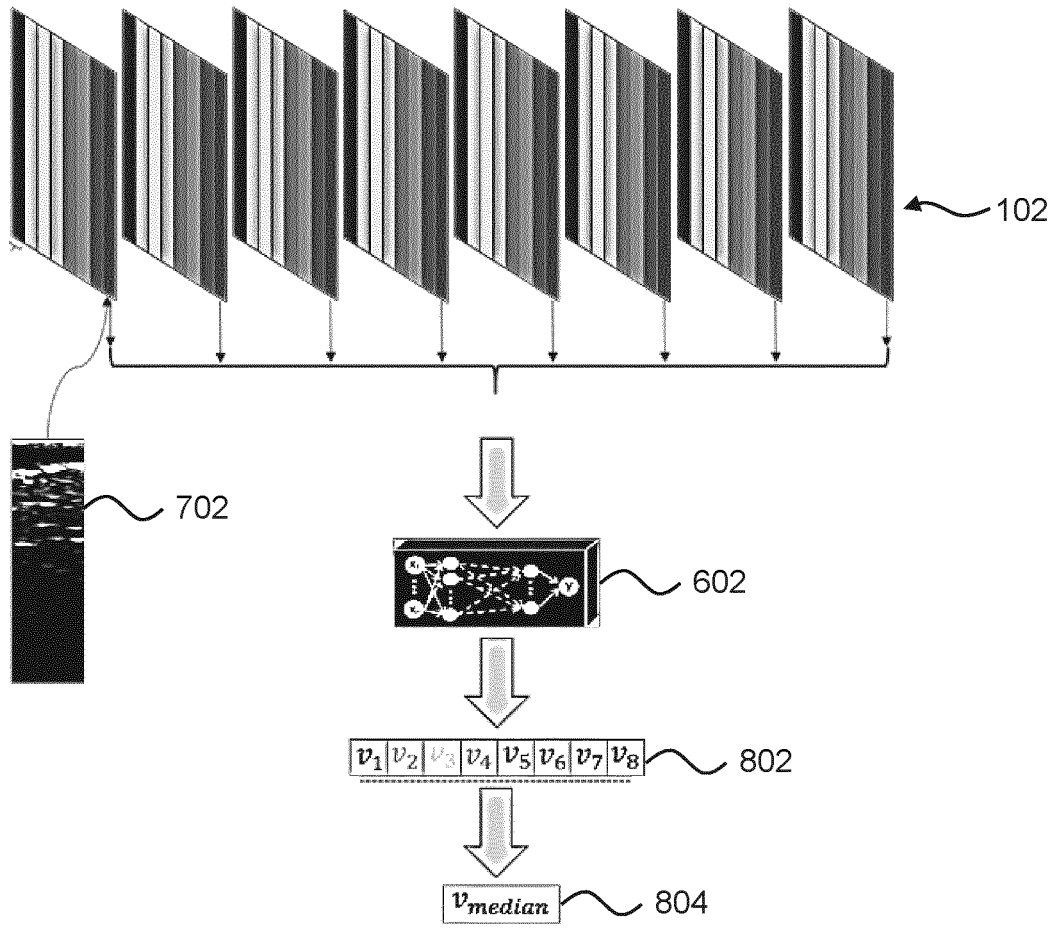
FIG. 8 shows a method for estimating the displacement from a plurality of images.

FIG. 8 shows a method for estimating the displacement from a plurality of images 102. In this example, there is a sequence of eight consecutive images 102, each divided into eight segments 702. Eight segments 702, corresponding to each one of the consecutive images 1102, are input into the machine learning algorithm 602 (e.g. a convolutional neural network) which outputs a sequence of estimated displacements 802 for each one of the input segments 702. The median of the eight output estimated displacements is given as the combined displacement estimate 804 for the center image(s) of the sequence of images 102 (i.e. images four and five, in this example).

In this example, the machine learning algorithm 602 may comprise multiple neural networks, each receiving a single segment 702 and outputting an estimated displacement for the single input segments 702. In some instances it may be beneficial to determine an estimated speed for each segment from the estimated displacements and the time difference in the input images 102 (e.g. from the known frame rate). Thus, a median speed estimate for the center image(s) can be determined from the estimated speeds instead of a median estimated displacement 804.

Figure 9:
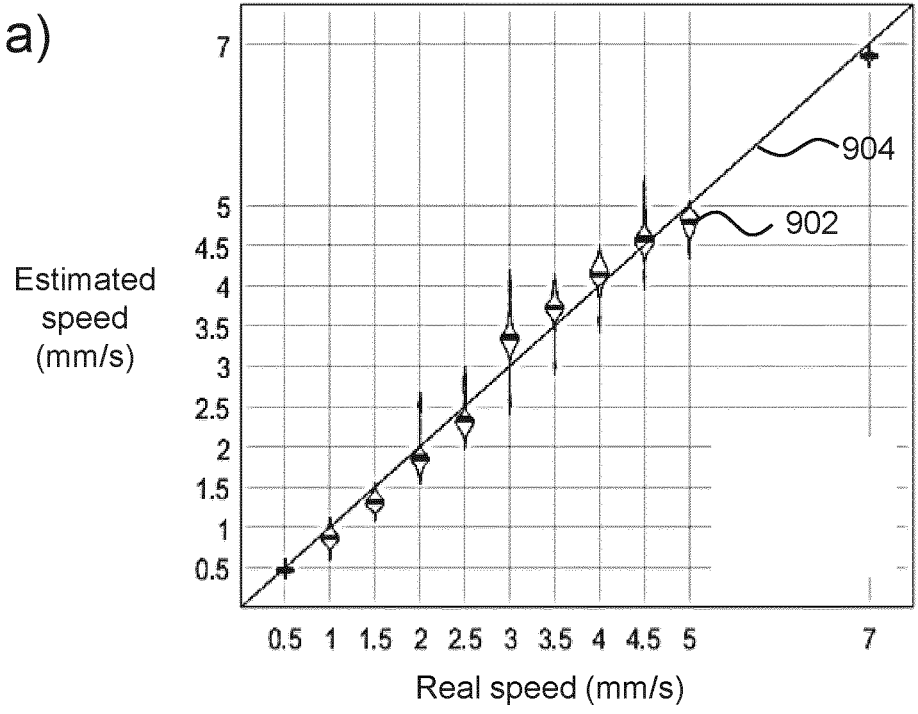
FIG. 9 shows test results for the use of a machine learning algorithm for estimating the speed of an interventional device in a lumen.
Figure 9:
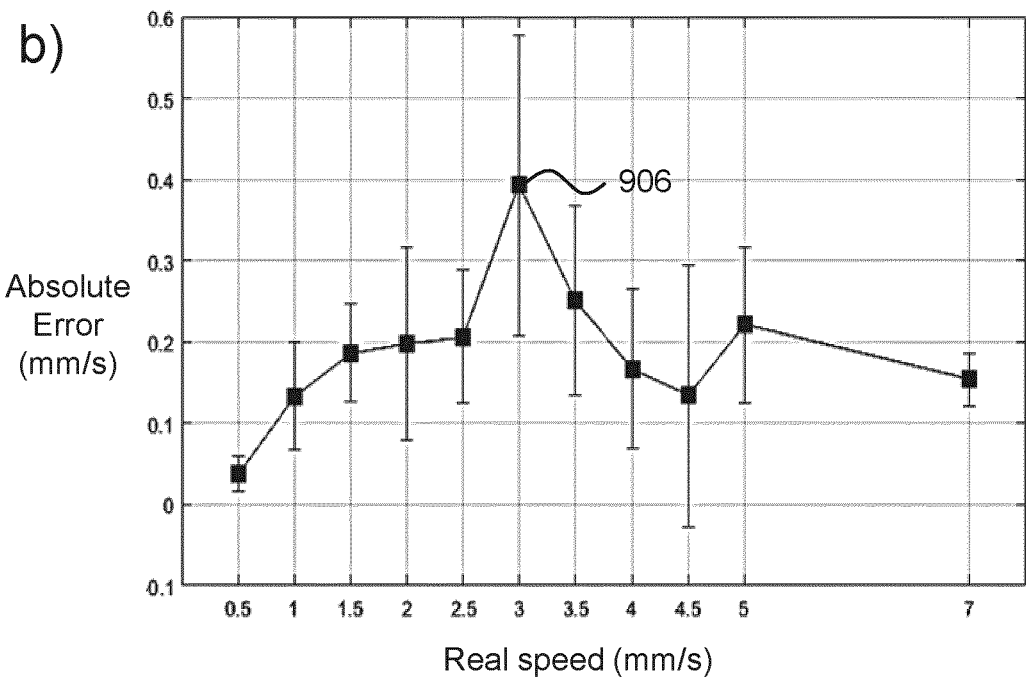

FIG. 9 shows test results for the use of a machine learning algorithm 602 for estimating the speed of a catheter in a lumen. The method for estimating the displacement shown in FIG. 8 was used for the test. FIG. 9a shows the estimated speed values in mm/s in the y-axis and the real speed values in mm/s in the x-axis. The estimated speed values can be determined from the estimated displacements and, for example, the frame rate of the images. Each point 902 in FIG. 9a shows the estimated speed obtained using the method shown in FIG. 8 against the real speed used to move the catheter. The line 904 shows the expected values if the estimated speed values were perfectly accurate. FIG. 9b shows mean absolute error between the estimated speed values and the real speed values in mm/s and the x-axis shows the real speed values in mm/s. Each point 906 shows the absolute difference between each point 902 and the corresponding point on the line 904.

Alternatively, two (or more) different machine learning algorithms can be been trained on different selections of training data, a method known as ensemble learning. Then, the median of the two or more separate estimated displacements can be used to generate a single, more robust displacement estimate. The ensemble learning method also exhibits a remarkable accuracy in estimating the real elevational displacement.

The relative stability of the speckle pattern and the predictable statistical properties has been exploited before to estimate motion between consecutive ultrasound frames. A known method is to use the correlation between consecutive images in combination with a regression model that describes the, generally non-linear, relation between the inter-frame correlation and the displacement. However, these methods of motion estimation are aimed at the use of external ultrasound probe and ignore the possible use of ultrasound transducers on the catheter itself (i.e. IVUS transducers).

Additionally, the correlation based methods of motion estimation assume the ultrasound transducer to be subject to a relatively large freedom of movement during the acquisition of the image sequence which increases the computational resources required to obtain an estimate and thus increase the time taken to obtain the estimate.

Figure 10:
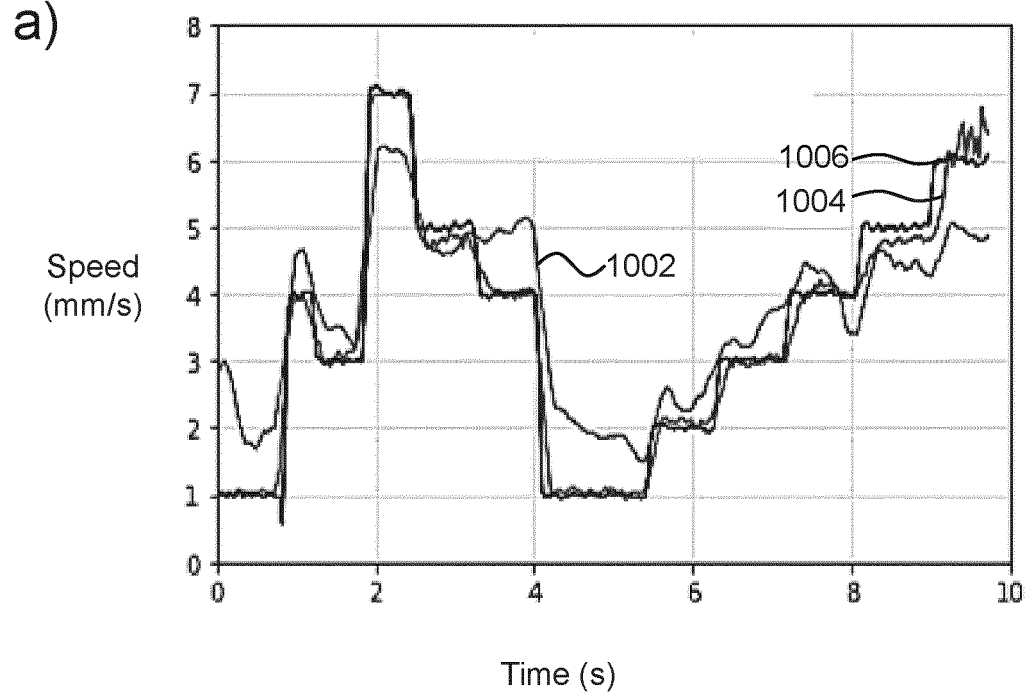
FIG. 10 shows the results for two methods of estimating the elevational speed of the interventional device and the real speed of the interventional device.
Figure 10:
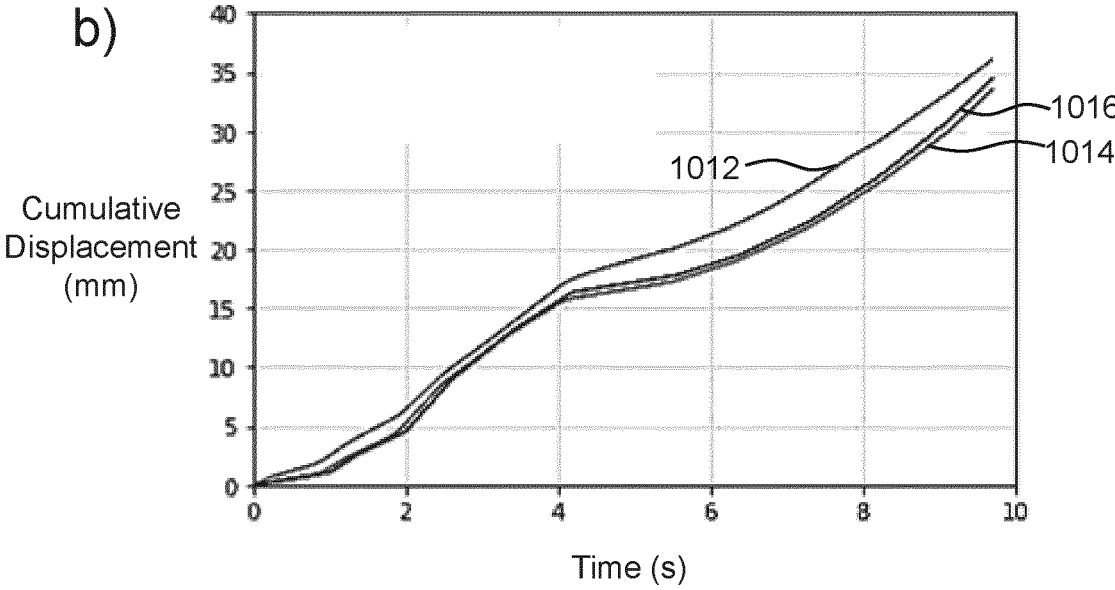

FIG. 10 shows the results for two methods of estimating the elevational speed of the catheter and the real speed of the catheter. The results depicted in FIG. 10a show the estimated speed obtained from the estimated displacements in line 1004 compared to the true (ground-truth) elevational speed in line 1006, acquired with a sufficiently accurate position detector, and further compared to speed estimates obtained from correlation-based speed estimation in line 1002. The y-axis shows the speed in mm/s and the x-axis shows the time in seconds.

FIG. 10b shows the cumulative displacement (i.e. the position relative to an origin) of the catheter obtained by integrating the three line 1002, 1004 and 1006 in FIG. 10a. The y-axis shows the cumulative displacement in mm and the x-axis shows the time in seconds. The line 1012 corresponds to the cumulative displacement estimated using the correlation-based method and is based on integrating line 1002. The line 1014 corresponds to the cumulative displacement estimated using the machine learning algorithm and is based on integrating line 1004. The line 1016 corresponds to the real cumulative displacement obtained by integrating line 1006. The accuracy of the correlation-based method is shown to be insufficient to accurately estimate the elevational displacement (and/or the elevational position) over longer distances. However, the estimation of the displacement by the machine learning algorithm exhibits a sustained position accuracy over longer longitudinal distances.

Recovery of relative image positions along the elevational direction can be used for depicting a sequence of automated area measurements as a function of elevational position and/or used for creating a 'motion-corrected' 3D tomographic reconstruction of the imaged anatomy The machine learning algorithm could also be trained with image sequences corresponding to speed values that exceed a theoretical resolution limit that is governed by the physical acquisition parameters (e.g. RF frequency and transducer shape).

Figure 11:
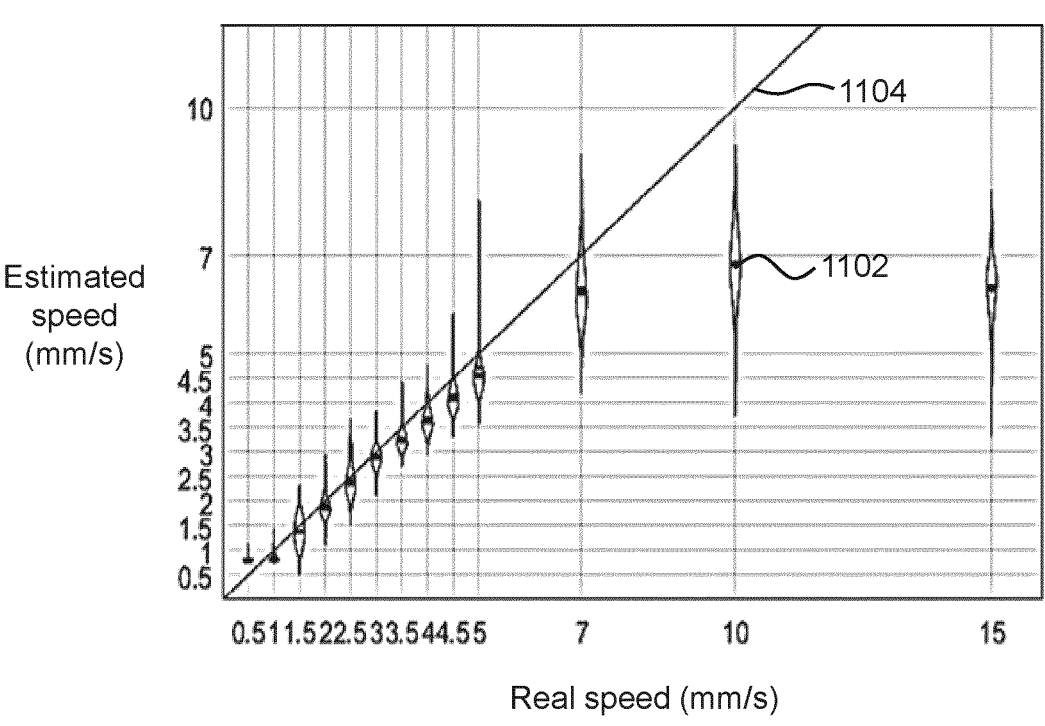
FIG. 11 shows test results for a machine learning algorithm trained with image sequences corresponding to speed values that exceed a resolution limit.

FIG. 11 shows test results for a machine learning algorithm trained with image sequences corresponding to speed values that exceed a resolution limit. The y-axis shows the estimated speed values obtained from the machine learning algorithm and the x-axis shows the real speed values. Each point 1102 shows the estimated speed obtained from using machine learning algorithm against the real speed used to move the catheter. The line 1104 shows the expected result if the estimated speed values had perfect accuracy.

Remarkably, without the machine learning algorithm having any knowledge of the physical resolution limits, it robustly produces speed estimates that saturate to a constant value (around 7 mm/s) when the overlap between consecutive slices becomes less than half the average speckle size in the elevational direction.

Thus, the machine learning algorithm can be used to provide an indication to the physician that the pullback speed is too high. In practice, this means that the spatial slices that are associated with consecutive frames do not sufficiently overlap to ensure a complete coverage of the imaged tissue.

The robust saturation behavior in speed estimation allows a relatively simple way to implement a feedback method for the operator of, for example, the IVUS catheter. For example, showing a 'green light' for values up to 5 mm/s, 'orange' for values between 5 mm/s and 6 mm/s, and 'red' for any value above 6 mm/s ('moving too fast'). These threshold values are an example based on the observation depicted in FIG. 11 obtained with an IVUS transducer that operate at 30 frames per second. For other catheters at different frequencies and framerates, different corresponding speed limits may also exists. With trained models for different catheters these speed limit indications could be offered to the physicians automatically.

Detection that the catheter speed exceeds a certain limit may invoke an indication to the operator too slow down and/or provide a signal to an algorithm indicating that continuity assumptions are violated (e.g. in a border segmentation algorithm).

Both the magnitude and direction in the elevational axis can be estimated with the machine learning algorithm, allowing the recovery of elevational frame locations under the presence of motion reversal. It is important to note that after motion reversal, the subsequent frame or frames will have to contain 'familiar' content, as the transducer essentially revisits old locations in the blood vessel. A possible approach is to determine the direction in the elevational axis is to use a so-called long-short-term-memory (LSTM) neural network.

Figure 12:
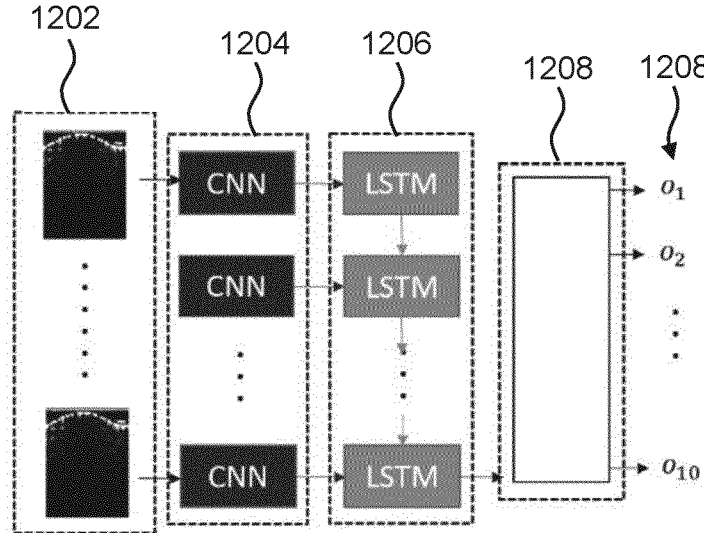
FIG. 12 shows an example machine learning algorithm for determining the direction of motion with an LSTM layer.

FIG. 12 shows an example machine learning algorithm for determining the direction of motion with an LSTM layer 1206. In this example, the LSTM layer 1206 is preceded by a convolutional neural network (CNN) 1204. Here, the CNN 1204 is trained to reduce each input image 1202 to a smaller feature vector while preserving the property to assess frame similarity. The LSTM 1206 is trained to provide an efficient comparison among previous frames. One or more dense layers 1208 are also trained to provide a classification 1208 for each input image 1202 indicating which images are acquired under reversed motion.

Optionally the LSTM-based motion direction estimator uses the magnitude of the estimated displacement as an additional input. The estimated direction and the estimated displacement can be used in combination for recovery of the relative image locations under a large variation of catheter and tissue motion.

Figure 13:
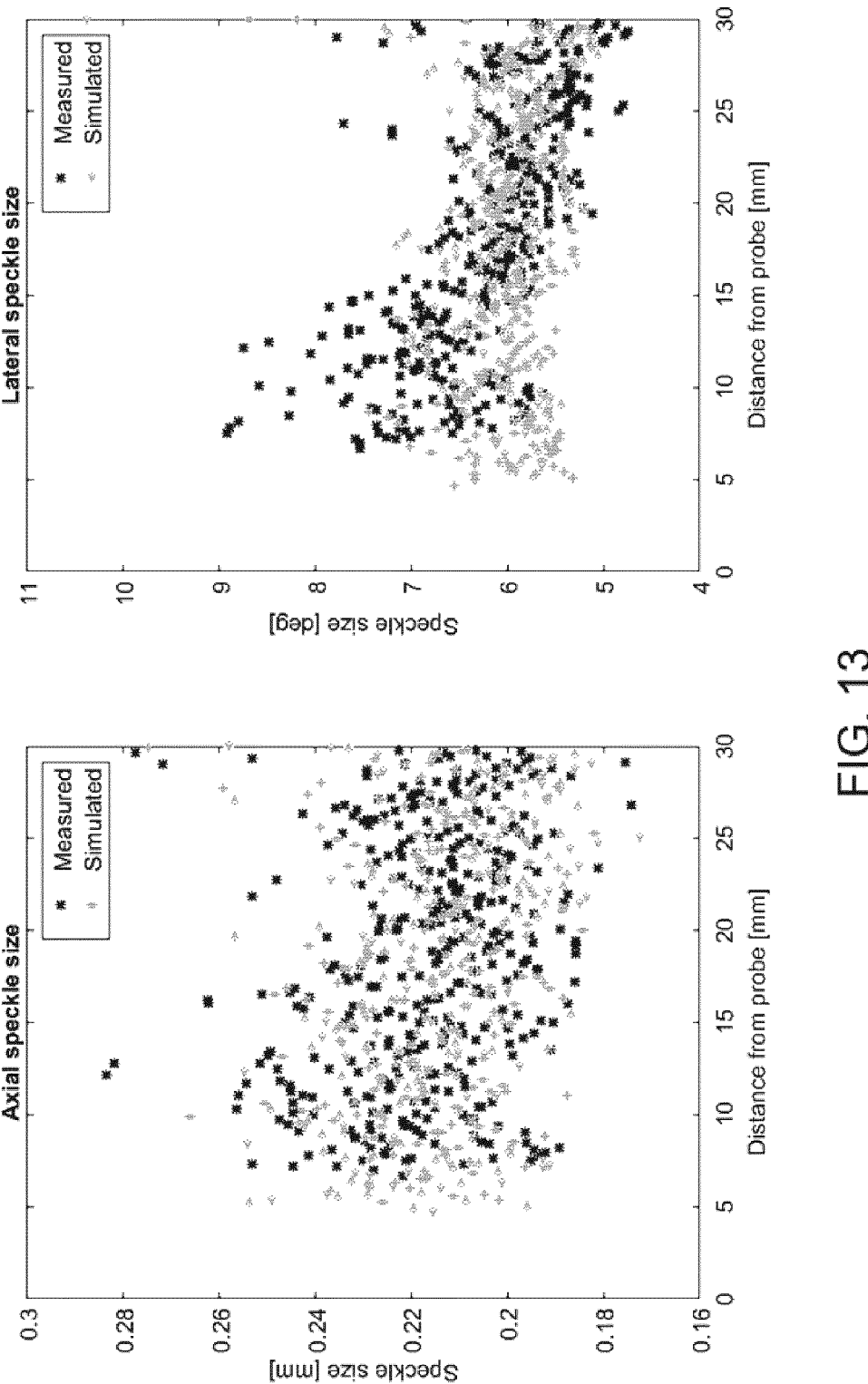
FIG. 13 shows speckle size in lateral, and axial direction.

The machine learning algorithm in any of the embodiments may be configured to accept IVUS images in polar representation instead of the Cartesian representation. Although the Cartesian representation provides a topologically correct shape- and size-preserving rendering of the anatomy, the polar representation provides a spatial domain in which the point-spread function of the image reconstruction becomes virtually space invariant. This beneficially causes the speckle pattern to adopt almost uniform statistical properties in both planar directions (in this case, a known average speckle size in lateral, and axial direction, the value of which can be calculated or measured). This is illustrated in FIG. 13. In case the speckle statistics are not uniform in space, e.g. showing a strong variation as a function of axial distance, this spatial distribution of the average speckle size is time invariant. Therefore, without loss of generality, we continue this discussion assuming a uniform speckle distribution. As far as such polar image representation is available as part of the complete image processing chain, the use of the image data in polar representation potentially benefits a computationally efficiency of the implementation and potentially minimizes the additional latency that is associated with the scan-conversion process that is required to display the IVUS images in Cartesian representation.

The machine learning algorithm may be further configured to determine the displacement between corresponding image regions between two or more consecutive images, giving rise to region-wise estimates of the local displacement in the longitudinal direction.

Figures 14, 15:
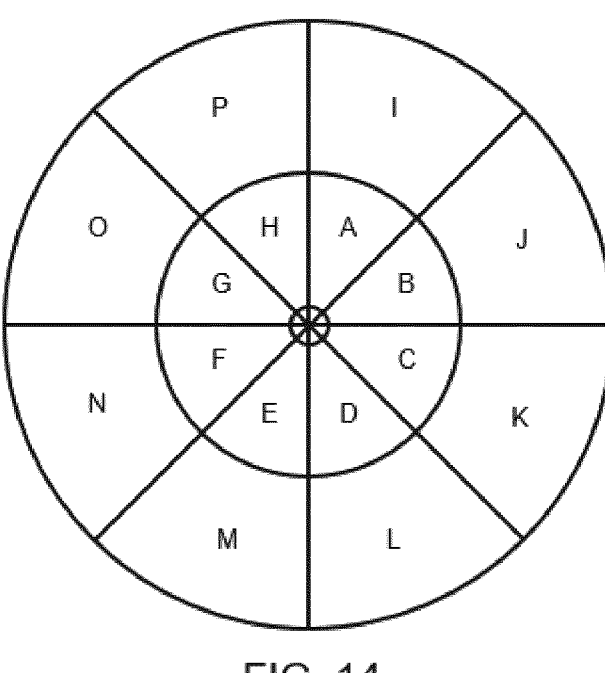
FIG. 14 and FIG. 15 representation in coordinates.

For example, these image regions can correspond to a sector of the IVUS image in Cartesian representation, beneficially corresponding to a rectangular region in polar representation. Additionally or alternatively, these image regions can correspond to different depth ranges, which correspond to rings in Cartesian representation, also beneficially corresponding to a rectangular region in polar representation. The combination is illustrated in FIG. 14 and FIG. 15.

The region-wise longitudinal displacement estimates may be combined to result in one single frame-wise displacement estimate. For example, in the case of sector-wise estimates, this allows the rejection of an estimation outlier among the set of estimations to increase the robustness of frame-wise estimates.

Figure 16:
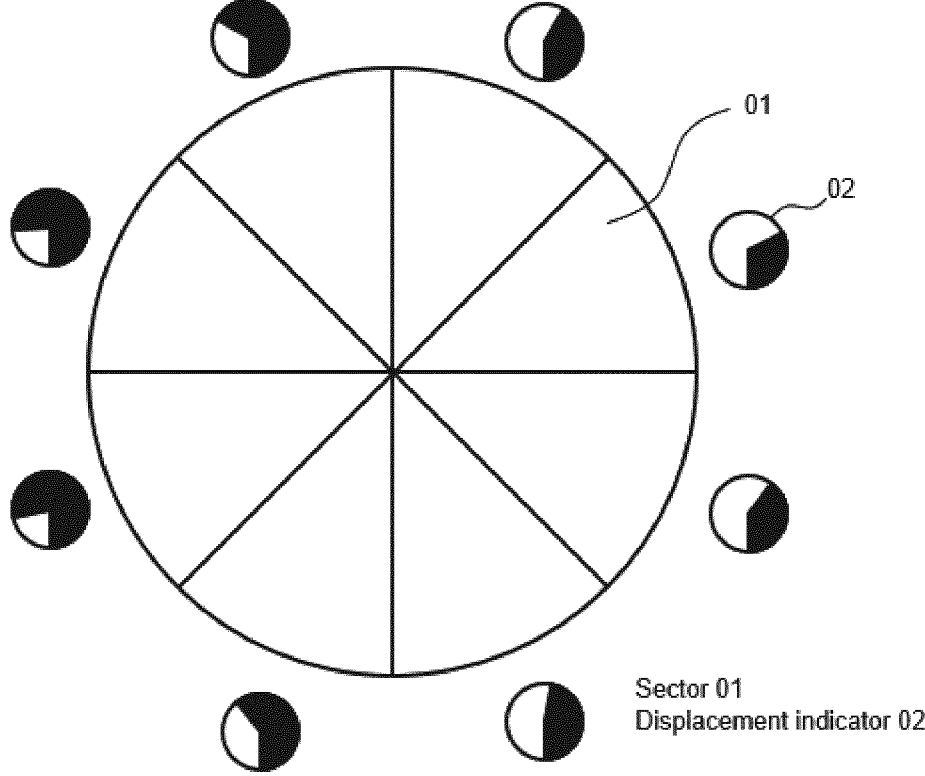
FIG. 16 and FIG. 17 representation of the displacement.
Figure 17:
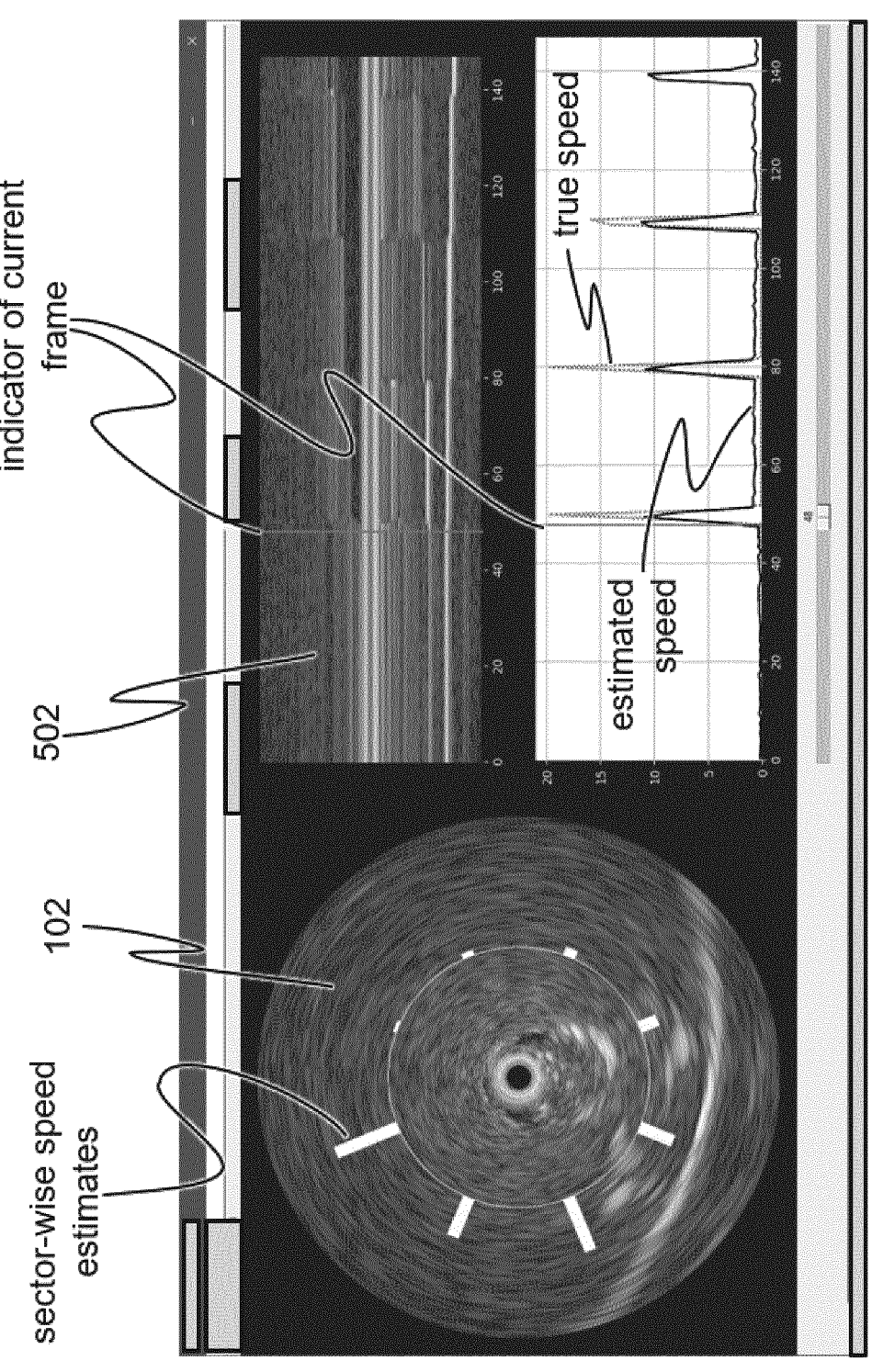

The region-wise longitudinal displacement estimates can beneficially enable displacement estimates corresponding to multiple time instances between the time instances associated with the sequence of completed frames. In phased-array IVUS, the image reconstruction itself tends to follow a rotating pattern which is associated with the order the channel data is acquired. Similar to mechanically rotating IVUS catheters, this causes consecutive image sectors to be associated different but consecutive time instances. Particularly in case the frame rate of IVUS images is relatively low, (typically associated to imaging of a large field-of-view), the temporal resolution associated with the frame instances can be insufficient to follow sudden changes in pullback speed. This is illustrated in FIG. 16 and FIG. 17.

Figure 18:
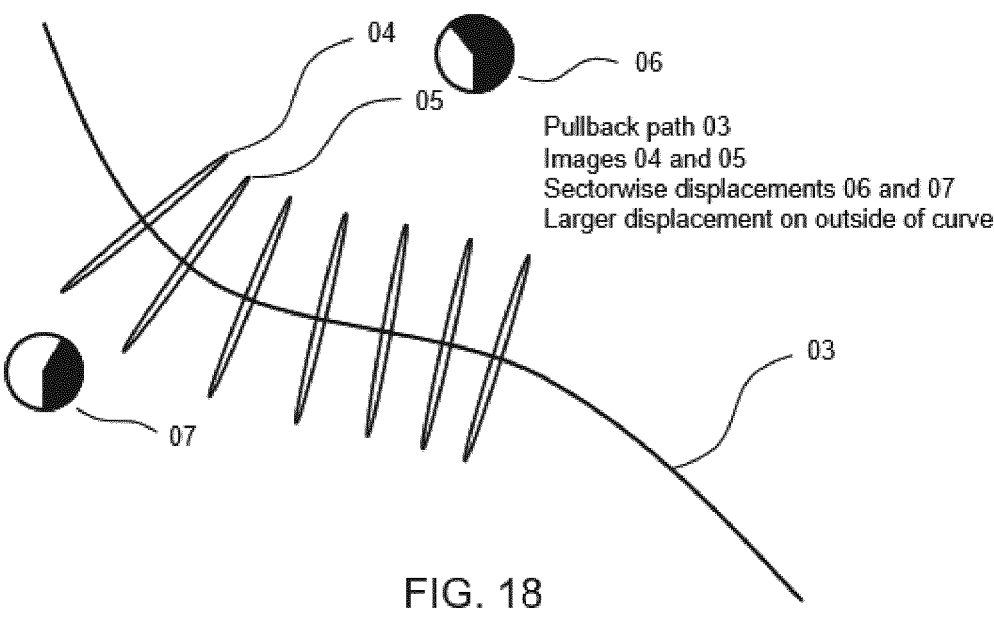
FIG. 18 shows the curvature of the pullback path.

The region-wise longitudinal displacement estimates may be combined to derive the curvature of the pullback path. For example, the region-wise estimates may be used to fit the parameters of a model (for example a planar model in the Cartesian domain). This is illustrated in FIG. 18.

For example, this sequence of curve estimates can be used to support the identification of anatomical landmarks.

Alternatively or additionally, this sequence of curve estimates can be used to compose an anatomically correct 3D representation of the vessel and surrounding tissue.

Figure 19:
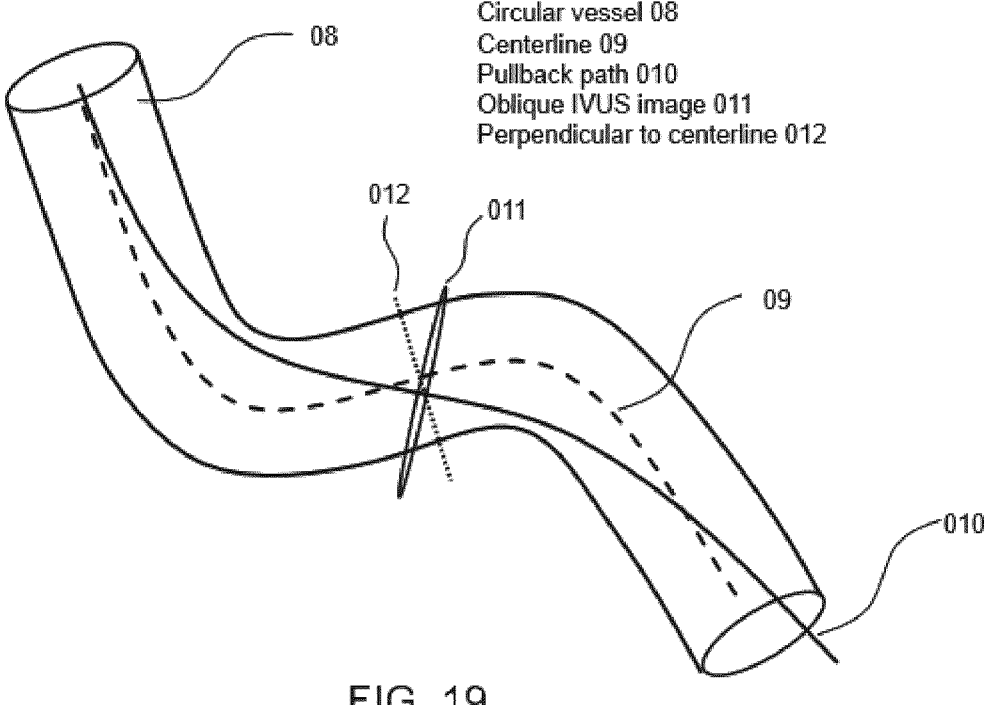
FIG. 19 shows vessel centerline, wherein the slices may cross the vessel under different oblique angles.

Alternatively or additionally, this sequence of curve estimates can be used to recover the true shape and diameter of the lumen from one or more IVUS images containing an oblique slice of the vessel. This may involve the composition of one or more (virtual) IVUS images, perpendicular to the longitudinal vessel centerline. This is illustrated in FIG. 19. This is analogous to extraction of a vessel centerline from CT slices, where the slices may cross the vessel under different oblique angles.

Figure 20:
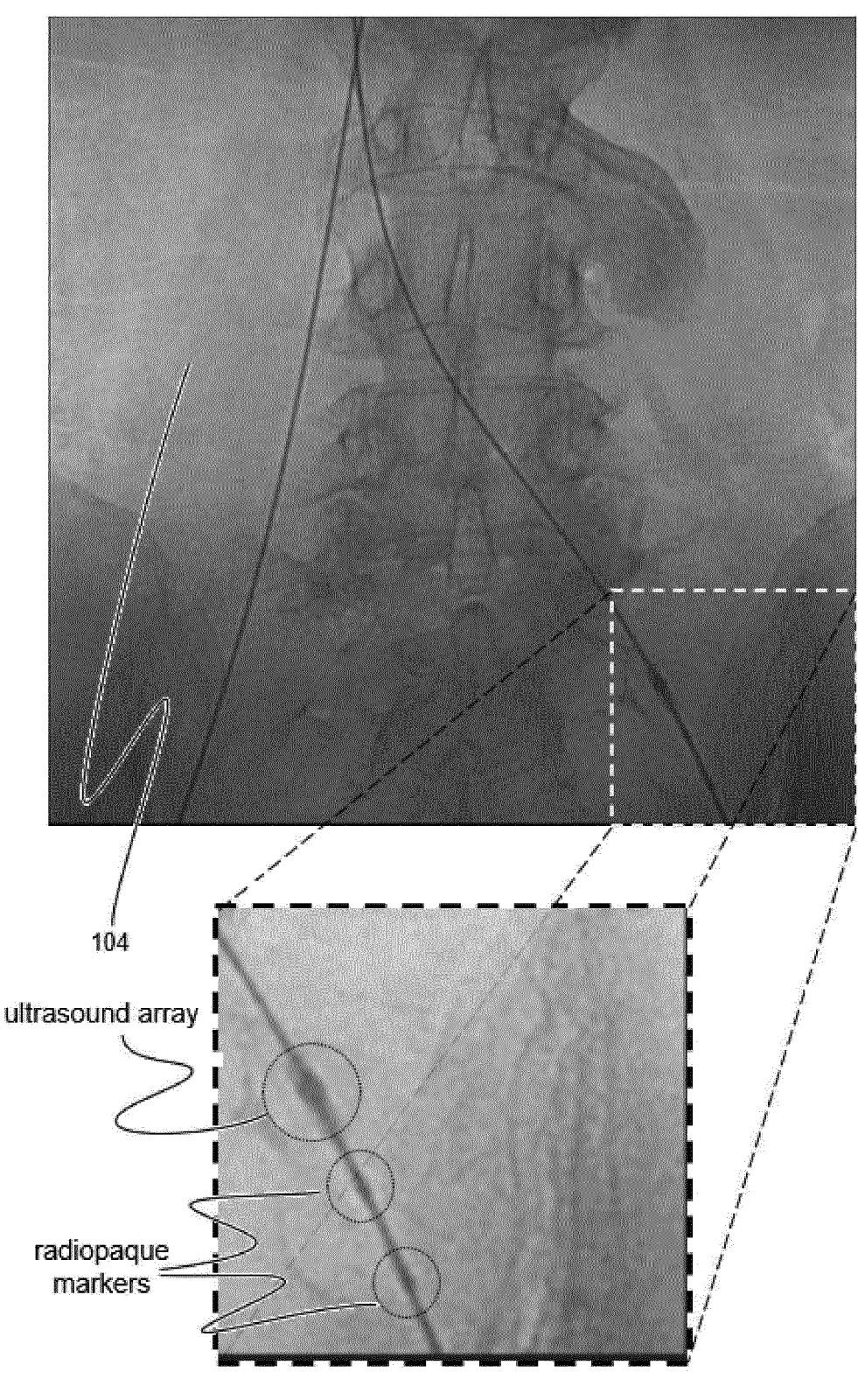
FIG. 20 shows X-ray image acquired simultaneously with the IVUS data.

Additionally, the recovery of the shape of the curved vessel may be aided by an extraluminal source of shape information, such as one or more X-ray images. Optionally, these X-ray images are acquired simultaneously with the IVUS data, showing (a projection of the catheter in relation to the anatomy). The catheter curvature within the projected plane provides a proxy for the true curvature in 3D. The perspective foreshortening of the projected radiopaque (uniformly spaced) markers on the catheter provides a proxy for the curvature out of the projection plane. Such markers are illustrated in FIG. 20. These sources of localized curvature information may be used to improve noisy or incomplete curvature estimates obtained from the IVUS data. In return the IVUS data may be used to improve the curvature estimates from the X-ray system, for instance to disambiguate the direction of the out-of-plane curvature derived from the X-ray images.

The machine learning algorithm may be further configured to accept one or more raw (channel) signals, intermediate signals, or intermediate representations of raw signals. Particularly in phase-array IVUS, the time interval between consecutive raw-signal acquisitions is much shorter that the time interval between consecutive frames. The higher time resolution between raw signals can be exploited to estimate catheter displacements under much higher pullback speeds, compared to the use of consecutive frames. As such, said used of raw or intermediate signals results in an intra-frame method for displacement estimation.

For example, the algorithm can use the set of time-of-flight-corrected (ToF) channel signals that are collected for the calculation of a beamformed A-line, associated with a radial collection of envelope values in the Cartesian B-mode output image. The number of the contributing (transmitting and receiving) consecutive array elements determines the size of the synthetic aperture with which the image is reconstructed. For instance, in case of delay-and-sum beamforming, these signals may exist in a signal buffer, prior to (weighted) summation and prior to envelope detection.

For example, these signals can be (re-)ordered according to their respective acquisition time instance. Here, a first signal-group and a second signal-group is composed, such that each contains one or more ToF-corrected channel signals, but such that the first and second group are associated with two different time instances. These signal groups can for instance be converted in a first and second envelope signal. A machine learning can be configured accept two or more of such signal-groups to produce an estimate of the catheter displacement during the time period between said signal groups. This estimate is associated with the radial line or radial lines associated with the location of the center of synthetic aperture. In case the IVUS catheter comprises an array of 64 elements, the above method would result in 64 displacement estimates per frame.

Returning to the acquisition of estimated displacements, the estimation of the displacement may be combined with information of the cardiac phase with the aim to ensure that (typically cyclic) cardiac-induced tissue deformations, (e.g. compression, translation, rotation) and associated measurements (e.g. lumen area) are not affecting the process that uses the spatially reordered images or the spatially reordered measurements. The cardiac phase information can come from an ECG device, be derived from an IVUS frame sequence, or be derived from the speed estimations.

The elevational displacement estimations (or an intermediate 3D spatial reconstruction) may also be used to support algorithms for e.g. side-branch detection or stent-segmentation.

Variations in elevational displacement between consecutive images can cause the anatomy and implants to appear deformed in the captured image sequence. Algorithms for automated detection potentially may benefit from knowledge of the elevational speed/displacement with which the images were acquired. Thus, a sequence of speed/displacement estimates may form an extra input to a detection or classification algorithm. Alternatively, the sequence of speed/displacement estimates can be used to perform intermediate motion correction of the corresponding images, after which the motion corrected images form the input to a detection or classification algorithm.

A machine-learning algorithm is any self-training algorithm that processes input data in order to produce or predict output data. Here, the input data comprises images from an ultrasound transducer and the output data comprises an estimate of the displacement of the catheter in a lumen in the elevational direction.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian models are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

An important aspect of training a machine learning algorithm to output displacement estimates is to ensure that the input images used for training contain similar speckle statistics to the real ultrasound images. This can be achieved by using, for example, a pullback engine for pulling the catheter and a phantom representation of a lumen in a body. A catheter moving in a lumen can also be simulated, thus snapshots of the simulation can be used as the training images.

The training input data entries correspond to example images from an ultrasound transducer. The training output data entries correspond to the estimated displacements.

The skilled person would be readily capable of developing a processor for carrying out any herein described method. Thus, each step of a flow chart may represent a different action performed by a processor, and may be performed by a respective module of the processing processor.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A system, comprising:
a processor configured to:
receive a plurality of intravascular images from an intravascular imaging catheter during movement of the intravascular imaging catheter through a lumen of a blood vessel along an elevational direction, wherein the intravascular imaging catheter is configured to obtain the one or more intravascular images along a radial direction perpendicular to the elevational direction, wherein the plurality of intravascular images are representative of the lumen;
input the plurality of intravascular images into a machine learning algorithm; and
output, by the machine learning algorithm, an estimated displacement of the intravascular imaging catheter in one dimension in real time during the movement, wherein the estimated displacement comprises units of distance, wherein the one dimension comprises the elevational direction,
wherein the machine learning algorithm is trained to determine a relationship between the plurality of intravascular images and the estimated displacement of the intravascular imaging catheter in the one dimension.

2. The system of claim 1,
wherein the intravascular imaging catheter comprises an ultrasound transducer is disposed on a distal portion of the intravascular imaging catheter, and
wherein an imaging plane of the ultrasound transducer is oriented along the radial direction such that the elevational direction is perpendicular to the imaging plane.

3. The system of claim 1,
wherein each intravascular image of the plurality of intravascular images has a corresponding acquisition time, and wherein the processor is further configured to determine an estimate of a speed of the intravascular imaging catheter based on the estimated displacement of the intravascular imaging catheter in the one dimension and a difference in the acquisition time between the plurality of images,
wherein the speed and the estimated displacement of the intravascular imaging catheter in the one dimension are distinct from one another.

4. The system of claim 1, wherein the processor is further configured to determine a position estimate of the intravascular imaging catheter in the lumen based on the plurality of intravascular images and the estimated displacement of the intravascular imaging catheter in the one dimension.

5. The system of claim 1, wherein the machine learning algorithm is configured to output a movement reversal indication that indicates a change in a direction of the movement of the intravascular imaging catheter within the lumen.

6. The system of claim 1, wherein the machine learning algorithm is configured to output the estimated displacement of the intravascular imaging catheter in the one dimension in at most 0.2 seconds from the plurality of intravascular images being input into the machine learning algorithm.

7. The system of claim 1, wherein the processor is further configured to determine a speed limit indication based on whether the estimated displacement of the intravascular imaging catheter in the one dimension is higher than a predetermined value.

8. The system of claim 1, wherein the machine learning algorithm is based on one or more of:
a fully connected neural network;
a convolutional neural network;
a recurrent neural network; or
a long short term memory (LSTM) based neural network.

9. The system of claim 1,
wherein the processor is further configured to split each intravascular image into a plurality of segments and input each segment into the machine learning algorithm, and
wherein the machine learning algorithm is further configured to output an estimated displacement for each segment.

10. The system of claim 1, wherein the processor is configured to:
output a plurality of estimated displacements of the intravascular imaging catheter in the one dimension; and
determine a median displacement indication from the plurality of estimated displacements.

11. The system of claim 1,
wherein the processor is further configured to input cardiac phase data into the machine learning algorithm,
wherein the cardiac phase data is representative of a subject's cardiac cycle.

12. The system of claim 1, further comprising a memory buffer for storing the plurality of intravascular images and/or storing the estimated displacement of the intravascular imaging catheter in the one dimension.

13. The system of claim 1, further comprising a user interface for displaying an intravascular image of the plurality of intravascular images and the estimated displacement of the intravascular imaging catheter in the one dimension that corresponds to the intravascular image.

14. A method, comprising:
receiving a plurality of intravascular images from an intravascular imaging catheter during movement of the intravascular imaging catheter through a lumen of a blood vessel along an elevational direction, wherein the intravascular imaging catheter is configured to obtain the one or more intravascular images along a radial direction perpendicular to the elevational direction, wherein the plurality of intravascular images are representative of the lumen;

inputting the plurality of intravascular images into a machine learning algorithm; and outputting, by the machine learning algorithm, an estimated displacement of the intravascular imaging catheter in one dimension in real time during the movement, wherein the estimated displacement comprises units of distance, wherein the one dimension comprises the elevational direction, wherein the machine learning algorithm is trained to determine a relationship between plurality of intravascular images and the estimated displacement of the intravascular imaging catheter in the one dimension.

15. A non-transitory computer-readable storage medium comprising computer program code which, when executed on a computing device having a processing system, cause the processing system to perform the steps of the method according to claim 14.

* * * * *